(12) United States Patent
Duncan et al.

(10) Patent No.: US 12,408,982 B2
(45) Date of Patent: *Sep. 9, 2025

(54) FRACTIONAL HANDPIECE SYSTEM

(71) Applicant: BIOLASE MG LLC, Foothill Ranch, CA (US)

(72) Inventors: Matt Duncan, San Clemente, CA (US); Justin Lanza, Orange, CA (US)

(73) Assignee: BIOLASE MG LLC

( * ) Notice: Subject to any disclaimer, the term of this patent is extended or adjusted under 35 U.S.C. 154(b) by 638 days.

This patent is subject to a terminal disclaimer.

(21) Appl. No.: 17/170,506

(22) Filed: Feb. 8, 2021

(65) Prior Publication Data

US 2021/0153937 A1    May 27, 2021

Related U.S. Application Data

(63) Continuation of application No. 16/113,803, filed on Aug. 27, 2018, now abandoned.

(Continued)

(51) Int. Cl.
*A61B 18/20* (2006.01)
*A61B 17/00* (2006.01)
(Continued)

(52) U.S. Cl.
CPC .......... *A61B 18/203* (2013.01); *A61C 1/0015* (2013.01); *A61C 1/0046* (2013.01);
(Continued)

(58) Field of Classification Search
CPC ................ A61B 18/203; A61B 18/22; A61B 2017/00199; A61B 2018/00029;
(Continued)

(56) References Cited

U.S. PATENT DOCUMENTS

| 4,337,040 A | 6/1982 | Cammack et al. |
| 4,711,630 A * | 12/1987 | Durr ...................... A61C 1/052 |
| | | 433/29 |

(Continued)

FOREIGN PATENT DOCUMENTS

| KR | 101677848 B1 | 11/2016 |
| WO | 1999007439 A1 | 2/1999 |
| WO | 2012040051 A1 | 3/2012 |

OTHER PUBLICATIONS

International Search Report for International Application No. PCT/US2018/048163, mailed Jan. 2, 2019, 7 pages.
(Continued)

*Primary Examiner* — Mark W. Bockelman

(57) ABSTRACT

An assembly with a handpiece assembly configured to receive electromagnetic energy and fluid, and to selectively deliver the electromagnetic energy and/or the fluid to a target surface. The handpiece assembly includes a handpiece housing and a plurality of fluid lines extending through the handpiece housing. The plurality of fluid lines can transfer fluid from a proximal end of the handpiece assembly to a distal end of the handpiece assembly. A spray mixer can be positioned at the distal end that is coupled to fluid lines of the plurality of fluid lines. An air input port can be positioned at the proximal end that is configured to be coupled to an auxiliary air hose, and an air delivery channel can be coupled to the air input port, and can supply air to a tip of an exchangeable applicator that can be coupled to the distal end of the handpiece housing.

20 Claims, 15 Drawing Sheets

Related U.S. Application Data

(60) Provisional application No. 62/550,509, filed on Aug. 25, 2017.

(51) Int. Cl.

| | | |
|---|---|---|
| *A61B 18/00* | (2006.01) | |
| *A61B 18/22* | (2006.01) | |
| *A61C 1/00* | (2006.01) | |
| *A61C 1/05* | (2006.01) | |
| *A61M 11/00* | (2006.01) | |
| *A61M 11/02* | (2006.01) | |
| *A61M 11/06* | (2006.01) | |
| *A61M 39/24* | (2006.01) | |

(52) U.S. Cl.
CPC ............ *A61M 11/02* (2013.01); *A61M 39/24* (2013.01); *A61B 2017/00199* (2013.01); *A61B 2018/00029* (2013.01); *A61B 2018/0047* (2013.01); *A61B 2018/202* (2013.01); *A61B 18/22* (2013.01); *A61B 2218/003* (2013.01); *A61B 2218/005* (2013.01); *A61C 1/0061* (2013.01); *A61C 1/052* (2013.01); *A61M 11/006* (2014.02); *A61M 11/06* (2013.01); *A61M 2039/2433* (2013.01); *A61M 2205/051* (2013.01); *A61M 2205/505* (2013.01)

(58) Field of Classification Search
CPC ...... A61B 2018/0047; A61B 2018/202; A61B 2218/003; A61B 2218/005; A61C 1/0015; A61C 1/0046; A61C 1/0061; A61C 1/052; A61M 11/02; A61M 39/24; A61M 11/006; A61M 11/06; A61M 2039/2433; A61M 2205/051; A61M 2205/505
See application file for complete search history.

(56) References Cited

U.S. PATENT DOCUMENTS

| | | |
|---|---|---|
| 5,092,864 A | 3/1992 | Hayes |
| 5,474,449 A | 12/1995 | Loge et al. |
| 5,825,958 A | 10/1998 | Gollihar et al. |
| 8,888,023 B2 | 11/2014 | Barton |
| 9,328,011 B2 * | 5/2016 | Washko, Jr. ....... B23K 26/0736 |
| 9,864,485 B2 | 1/2018 | Patton |
| 2006/0121411 A1 | 6/2006 | Wiek et al. |
| 2008/0276192 A1 | 11/2008 | Jones |
| 2012/0136383 A1 | 5/2012 | Boutoussov et al. |
| 2014/0257254 A1 | 9/2014 | Boutoussov |
| 2015/0268803 A1 | 9/2015 | Patton |
| 2019/0105140 A1 * | 4/2019 | Berkely ................ A61B 1/247 |

OTHER PUBLICATIONS

Written Opinion for International Application No. PCT/US2018/048163, mailed Jan. 2, 2019, 6 pages.

\* cited by examiner

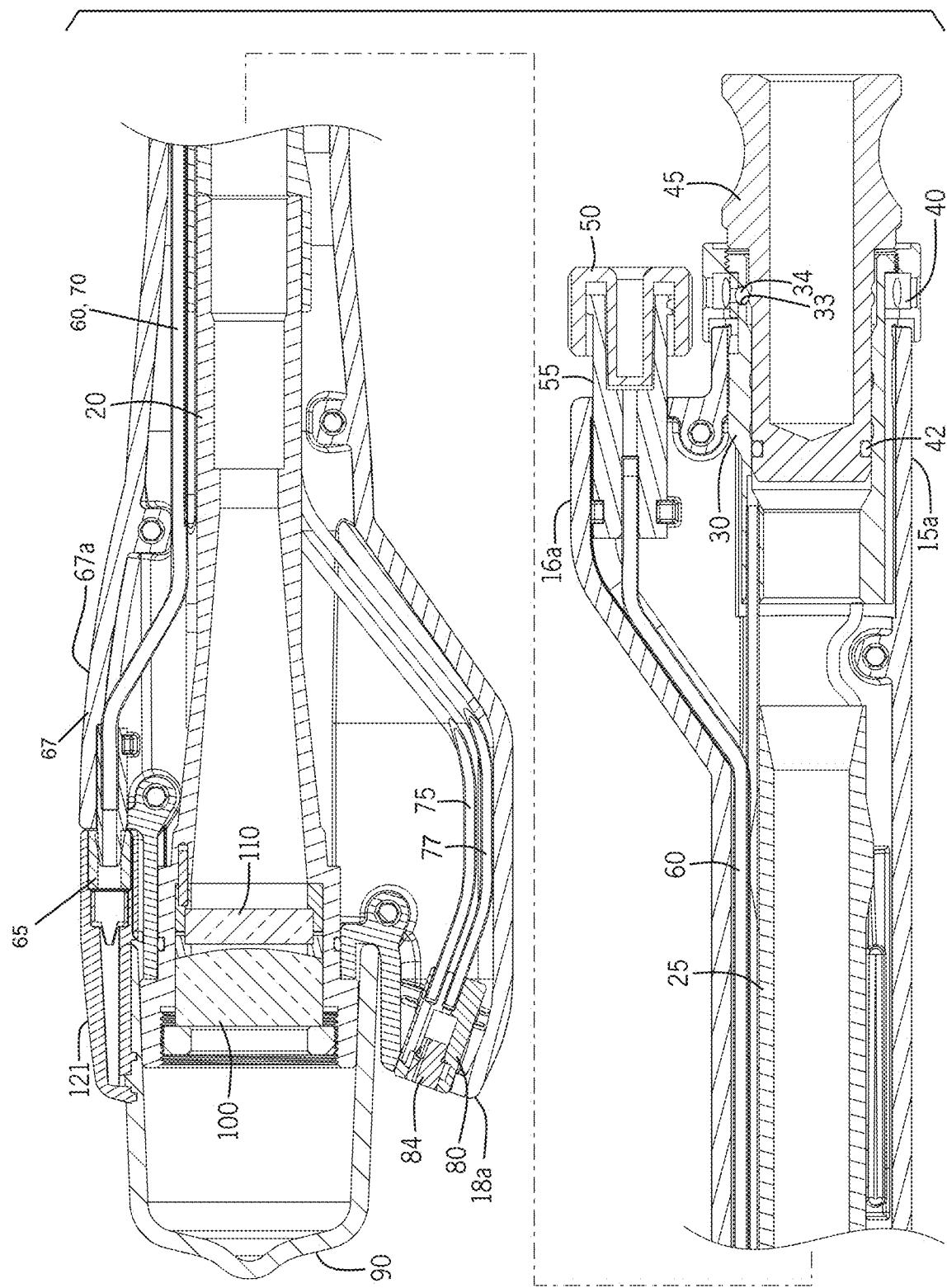

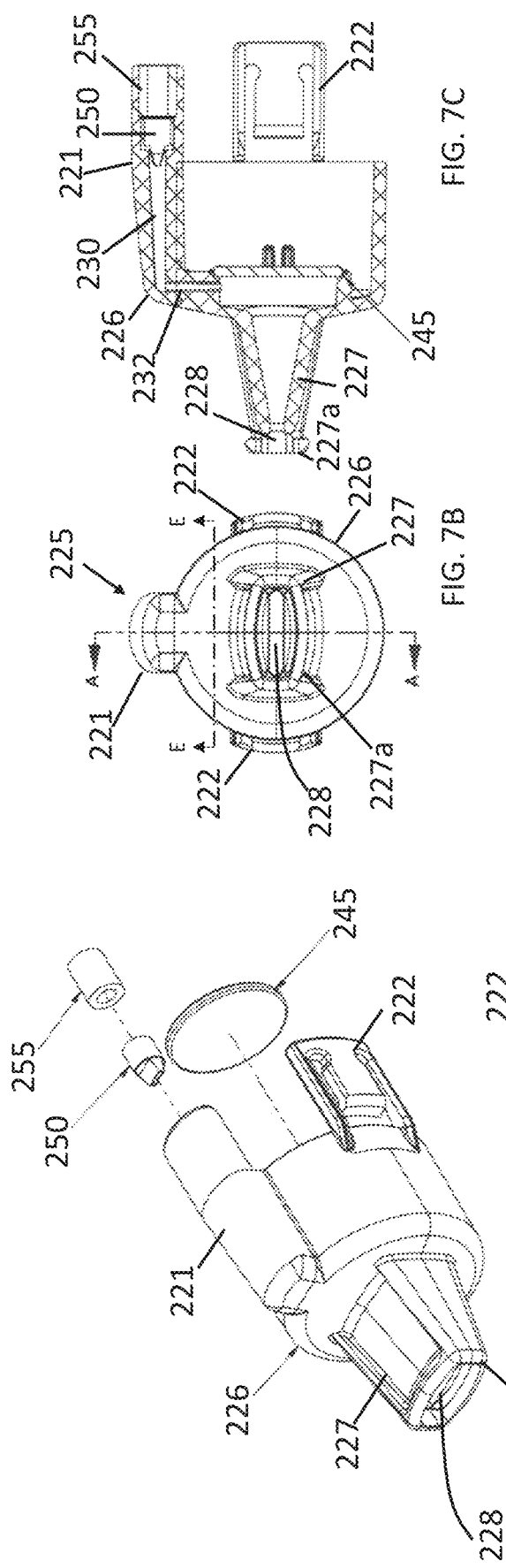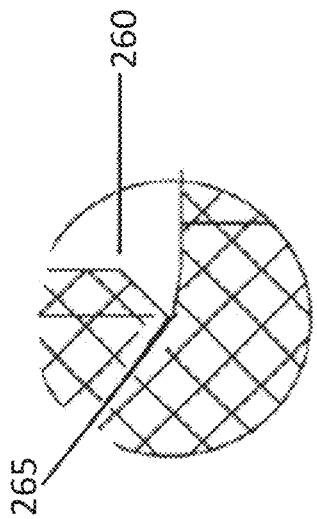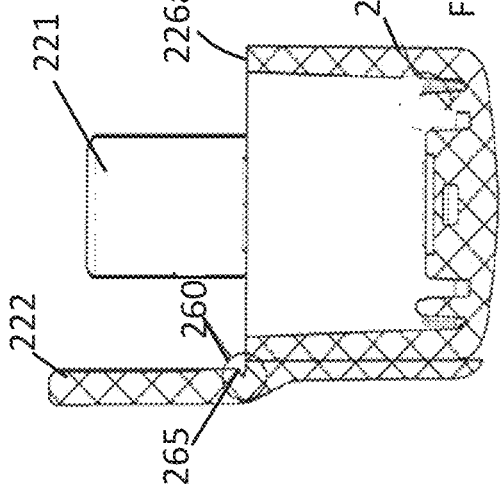

FRACTIONAL HANDPIECE SYSTEM

RELATED APPLICATIONS

This patent application claims the benefit of and is a continuation of co-pending U.S. Publication Ser. No. 16/113,803, filed on Aug. 27, 2018, which claims the benefit of priority to U.S. Provisional Application Ser. No. 62/550,509, filed on Aug. 25, 2017, which are incorporated by reference herein in their entirety.

BACKGROUND

A conventional medical handpiece typically includes a waveguide (e.g., a fiber optic or trunk fiber) coupled to a laser housing or module that provides electromagnetic (e.g., laser) energy that can be directed to a target surface such as bone, skin, dental tissue, or other biological surface. Some medical procedures utilize water spray, mist or vapor and/or air or other inert gas in combination with a laser pulse to enhance treatment efficacy. Some medical procedures benefit from (or require) disposable applicator tips that can be used in close proximity to, or in contact with, the patient's tissue during treatment, and disposed of after use. The ergonomic packaging of supply lines and delivery nozzles for air and water within a handpiece that maintains an ability to enable swift and user-friendly exchange of disposable applicator tips remains a challenge from a design, manufacturing, and cost perspective.

SUMMARY OF THE INVENTION

Some embodiments include an assembly comprising a handpiece assembly configured to receive and electromagnetic energy and at least one fluid, and to selectively deliver at least one of the electromagnetic energy and the at least one fluid to a target surface. In some embodiments, the handpiece assembly comprises a handpiece housing and a plurality of fluid lines extending through the handpiece housing. In some embodiments, the plurality of fluid lines can transfer at least one fluid from a proximal end of the handpiece assembly to a distal end of the handpiece assembly. Some embodiments include a spray mixer positioned at the distal end that is coupled to fluid lines of the plurality of fluid lines. Some further embodiments include an air input port positioned at the proximal end that is configured to be coupled to an auxiliary air hose Some embodiments include an air delivery channel coupled to the air input port and that can supply air to a tip of an exchangeable applicator configured to be coupled to the distal end of the handpiece housing.

In some embodiments, the assembly further comprises a disposable applicator comprising at least one structure configured and arranged to weaken or have reduced mechanical strength or integrity of at least one coupler or clip extending from a main body of the disposable applicator. The at least one coupler or clip is configured and arranged to at least partially secure the disposable tip to the distal end of the handpiece assembly.

In some embodiments, the at least one structure comprises a notch. In some embodiments, the notch is positioned at an edge of the main body and extends at least partially into the at least one coupler or clip, where the at least one coupler or clip is configured by the notch to break from the main body when a user removes the disposable applicator from the handpiece assembly.

Some embodiments include a system comprising a laser delivery system configured to deliver electromagnetic energy via a fiber optic cable. Some embodiments include a handpiece assembly configured to be coupled to the fiber optic cable to receive the electromagnetic energy. In some embodiments, the handpiece assembly is configured to receive at least one fluid and to selectively deliver at least one of the electromagnetic energy and the at least one fluid to a target surface. In some embodiments, the handpiece assembly comprises a spray mixer positioned at a distal end of the handpiece assembly, and coupled to fluid lines of the plurality of fluid lines.

Some embodiments include an air input port positioned at a proximal end of the handpiece assembly, and configured to be coupled to an auxiliary air hose. Some further embodiments include an air delivery channel coupled to the air input port and configured to supply air to the target surface via an exchangeable coupled disposable applicator.

Some embodiments of the invention include a GUI display communicatively linked to or included in the laser delivery system. The GUI display is configured to display at least one operating status or selectable parameter of the handpiece assembly.

Some embodiments include a processor and a non-transitory computer-readable storage medium in data communication with the processor. The non-transitory computer-readable storage medium includes a process executable by the processor that enables a user to interact with the GUI to select or change one or more one or more settings or parameters and/or monitor one or more functions of the handpiece assembly.

In some embodiments, one or more one or more settings or parameters of the handpiece assembly include at least one of a laser power, and a laser pulse width. In some embodiments, the one or more one or more settings or parameters of the handpiece assembly comprises at least one selectable favorite selected from a GUI comprising a favorites selection window or icon. In some further embodiments, the one or more one or more settings or parameters of the handpiece assembly comprises at least one selectable category selected from a GUI comprising a category selection window.

In some embodiments, the GUI comprises a spray parameter display configured for displaying and/or controlling spray parameters of the handpiece assembly. In some embodiments, the GUI includes a power meter with selectable power level, and/or a laser mode display and/or selector, and/or a selectable slider configured for modifying and/or setting at least one parameter of a procedure, and/or a pulse display with selectable pulse icon.

In some embodiments of the invention, the GUI includes an air delivery display with air setting and/or air mode. In some further embodiments, the GUI includes a water delivery display with water setting, and water mode icon. In some embodiments, the GUI includes an auxiliary icon configured for selecting or indicating auxiliary components and/or sources providing air and/or water. In some other embodiments, the GUI includes a handpiece exchange icon and/or tip exchange icon configurable to install and/or swap a handpiece and/or tip of the handpiece assembly.

In some embodiments of the invention, the disposable applicator comprises at least one structure configured and arranged to weaken or reduce the mechanical strength or integrity of at least one coupler or clip extending from a main body of the disposable applicator. The at least one coupler or clip is configured and arranged to at least partially secure the disposable tip to the distal end of the handpiece assembly. In some embodiments of the system, the at least one structure comprises a notch.

In some embodiments of the system, the notch is positioned at an edge of the main body of the disposable applicator, and extends at least partially into the at least one coupler or clip, where the at least one coupler or clip is configured by the notch to break from the main body when a user removes the disposable applicator from the handpiece assembly.

In some embodiments, the spray mixer is positioned in a lower housing extension that curves inward so that an output of the spray mixer is guided towards an axial center of the handpiece assembly. In some embodiments, the disposable applicator comprises a valve configured to couple to a connector at the distal end of the handpiece assembly. In some embodiments, the valve comprises a duckbill valve.

DESCRIPTION OF THE DRAWINGS

FIG. 4 illustrates a cross-sectional view of the handpiece assembly of FIG. 1 in accordance with some embodiments of the invention.

FIG. 7A illustrates an assembly view of a disposable applicator tip in accordance with some embodiments of the invention.

FIG. 7B illustrates a front view of the disposable applicator tip of FIG. 7A in accordance with some embodiments of the invention.

FIG. 7C illustrates a cross-section view through "A" of the disposable applicator tip of FIG. 7B in accordance with some embodiments of the invention.

FIG. 7D illustrates a cross-section view through "E" of the disposable applicator tip of FIG. 7B in accordance with some embodiments of the invention.

FIG. 7E illustrates a close-up view of the notch shown in FIG. 7D in accordance with some embodiments of the invention.

DETAILED DESCRIPTION

Figure 1:
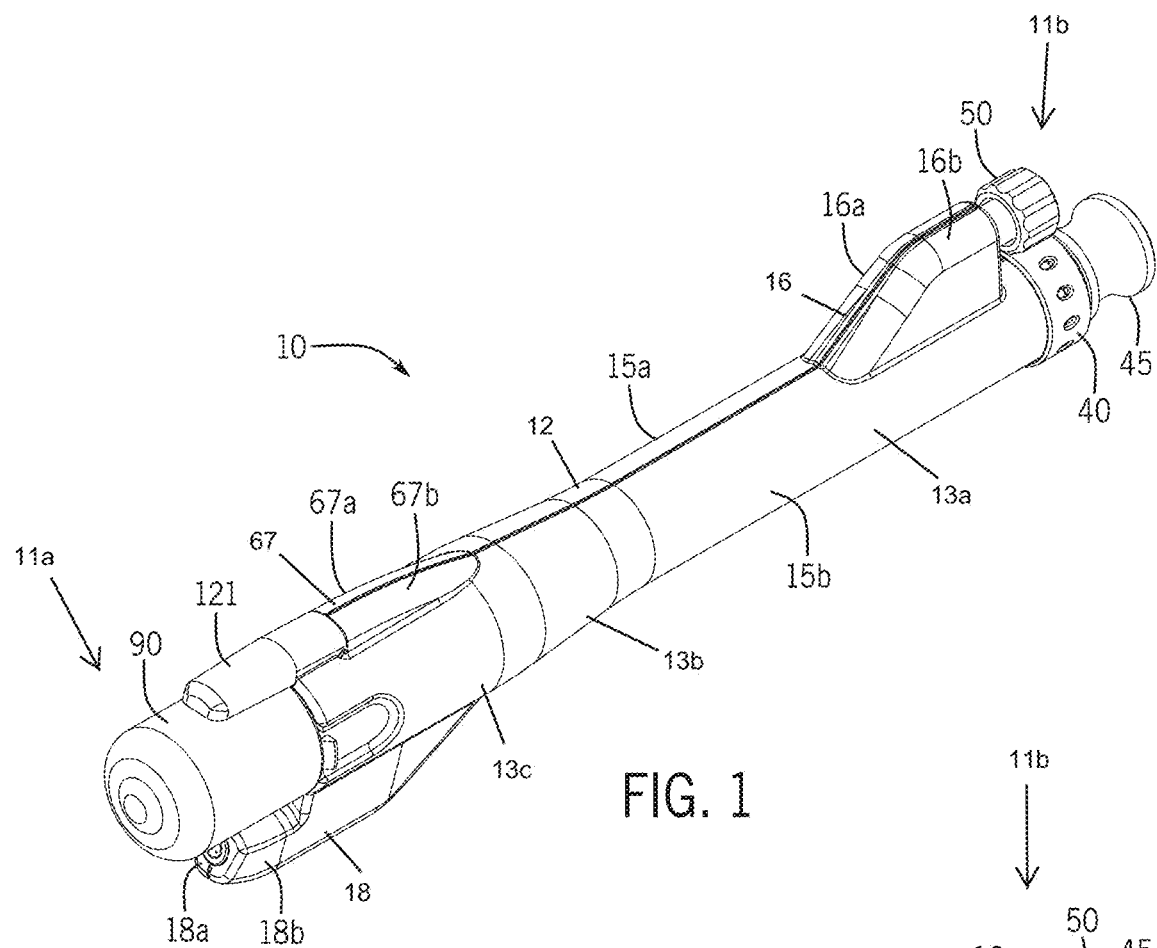
FIG. 1 illustrates a perspective view of a handpiece assembly in accordance with some embodiments of the invention.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings.

The following discussion is presented to enable a person skilled in the art to make and use embodiments of the invention. Various modifications to the illustrated embodiments will be readily apparent to those skilled in the art, and the generic principles herein can be applied to other embodiments and applications without departing from embodiments of the invention. Thus, embodiments of the invention are not intended to be limited to embodiments shown, but are to be accorded the widest scope consistent with the principles and features disclosed herein. The following detailed description is to be read with reference to the figures, in which like elements in different figures have like reference numerals. The figures, which are not necessarily to scale, depict selected embodiments and are not intended to limit the scope of embodiments of the invention. Skilled artisans will recognize the examples provided herein have many useful alternatives that fall within the scope of embodiments of the invention.

The various embodiments of the invention described herein include devices, apparatus, systems and methods to enable the use and control and/or monitoring of complex dental laser procedures. Further, some embodiments of the invention can include control systems, displays, and associated user interfaces that can be used to control some aspect of a dental laser system, and/or communicate some function or operational characteristic of the tool to the user. For example, some embodiments can include control systems, displays, and user interfaces that can be used to perform procedures related to dental restoration and oral disease prevention. More specifically, some embodiments of the invention described herein include devices, apparatus, systems and methods to enable a user to operate and/or monitor the functional aspects of dental laser systems using interfaces that can be customized for a specific dental procedure and/or for any specific dental specialty including, but not limited to general dentistry, oral and maxillofacial dentistry, orthodontic dentistry, endodontic dentistry, pediatric dentistry, cosmetic dentistry, and so on.

Some embodiments include a handpiece configured to operate with one or more specific lasers. Further, some embodiments include water atomization technologies that can be used during laser use. Some embodiments include a handpiece configured to function with a specific tissue laser and water atomization technologies to ablate skin and/or reshape soft tissue with minimal trauma and maximum efficacy. For example, in some embodiments, the handpiece can function to provide skin resurfacing, and scar revision including acne scarring, and treatment of wrinkles. In reference to FIG. 1, showing a perspective view of a handpiece assembly 10, some embodiments include a handpiece assembly 10 that includes a longitudinal housing 12 formed from the coupling of a left-side shell 15a to a right-side shell 15b extending from a distal end 11a to a proximal end 11b. In some embodiments, the housing 12 can comprise a generally cylindrical first body portion 13a extending from the proximal end 11b to a transition body region 13b that begins about half-way along the longitudinal length of the housing 12, and extends towards second body portion 13c extending to the distal end 11a.

In some other embodiments, the longitudinal housing 12 can be assembled using more than two halves (e.g., where the left-side shell 15a and right-side shell 15b represent two halves in the non-limiting embodiment, but could be shaped to comprise two portions capable of coupling to one or more additional portions to form the housing 12). In some embodiments, the shells 15a, 15b and/or any additional or other portions forming the housing 12 can be permanently coupled. In some other embodiments, the shells 15a, 15b and/or any additional or other portions forming the housing 12 can be reversibly coupled.

In some embodiments, the housing 12 can include various extensions and/or compartments configured to house one or more accessories and/or various inputs and/or outputs (e.g., such as inputs and outputs for air and fluid and/or mixtures thereof). For example, some embodiments include an upper housing extension 16 comprising a left-side 16a and right-side 16b extending from the first body portion 13a of the housing 12 adjacent the proximal end 11b. Some further embodiments include a lower housing extension 18 comprising a left-side 18a and right-side 18b extending in an opposite direction to the upper housing extension from the second body portion 13c of the distal end 11a. In some other embodiments of the invention, the handpiece assembly 10 includes a housing extension 67 comprising a left-side 67a and right-side 67b extending in an opposite direction to the lower housing extension 18 and generally positioned on the opposite side of the second body portion 13c adjacent the distal end 11a. In some embodiments, any one or more of the extensions 16, 18, 67 can be coupled to the housing 12. In other embodiments, any of the extensions 16, 18, 67 can be integral to the housing 12.

In some embodiments of the invention, the upper housing extension 16 can include a conventional linkage or coupling that can enable the reversible coupling of a fluid input. For example, in some embodiments, the upper housing extension 16 can include a luer lock coupling 50 that can enable the coupling of the handpiece assembly to an auxiliary air input. In some embodiments, the luer lock coupling 50 can extend from the upper housing extension 16 towards the proximal end 11b and generally axially aligned with longitudinal length of the housing 12. In some embodiments, the proximal end 11b of the first body portion 13a of the housing 12 can include a plug 45 coupled to the proximal end 11b adjacent an exhaust 40.

Some embodiments include an air coupler housing 121 extending from the distal end 11a and coupled to the housing extension 67. In some embodiments, the air coupler housing 121 can enable coupling of air or other gas to the handpiece assembly 10 by an air delivery line (not shown) for providing a supply of on-demand air. In some further embodiments, the air coupler housing 121 can be couple to, or integrated with, a disposable applicator (see below in related to FIGS. 7A-7E).

Figure 2:
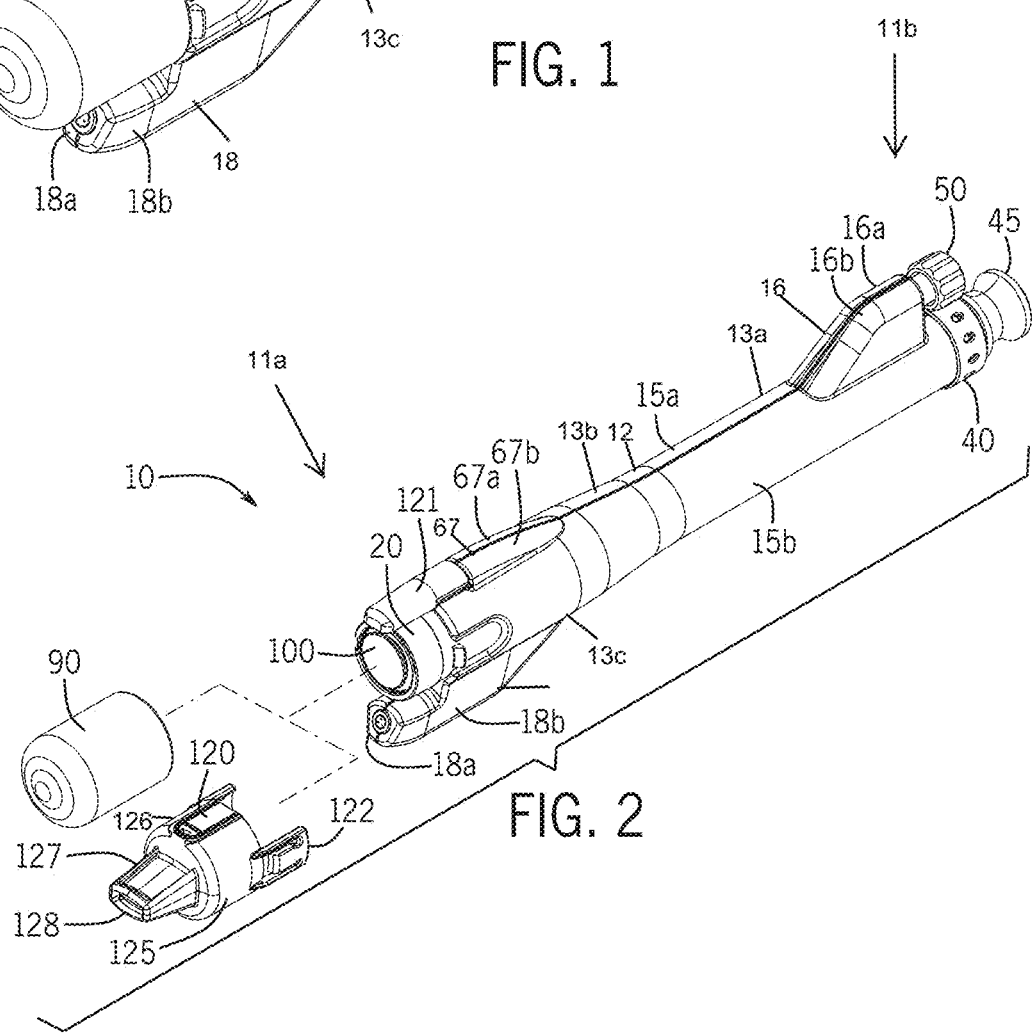
FIG. 2 illustrates an assembly view of the handpiece assembly of FIG. 1 in accordance with some embodiments of the invention.

Some embodiments of the invention include a protective lens cap 90 positioned coupled to and extending from the distal end 11a. In some embodiments of the invention, the protective lens cap 90 can be coupled to the housing 12 during periods of storage and non-use, and can be removed prior to use and/or when installing an applicator tip. In reference to FIG. 2, illustrating an assembly view of the handpiece assembly 10 of FIG. 1 in accordance some embodiments of the invention, the handpiece assembly 10 can include an applicator 125. In some embodiments, the cap 90 and applicator 125 are interchangeable or swappable components of the handpiece assembly 10. In other words, in some embodiments, the handpiece assembly 10 can comprise the cap 90, and in other embodiments, the handpiece assembly 10 can comprise the applicator 125. As shown in FIG. 2, in some embodiments, the distal end 11a of the housing 12 can include an optical housing 20 (showing the distal end). In some embodiments, the cap 90 and/or the applicator 125 can couple to the optical housing 20. In some further embodiments, the housing assembly 10 can include other peripheral attachments, accessories, covers, and stands or supports as needed and/or selected by a user.

Figure 3:
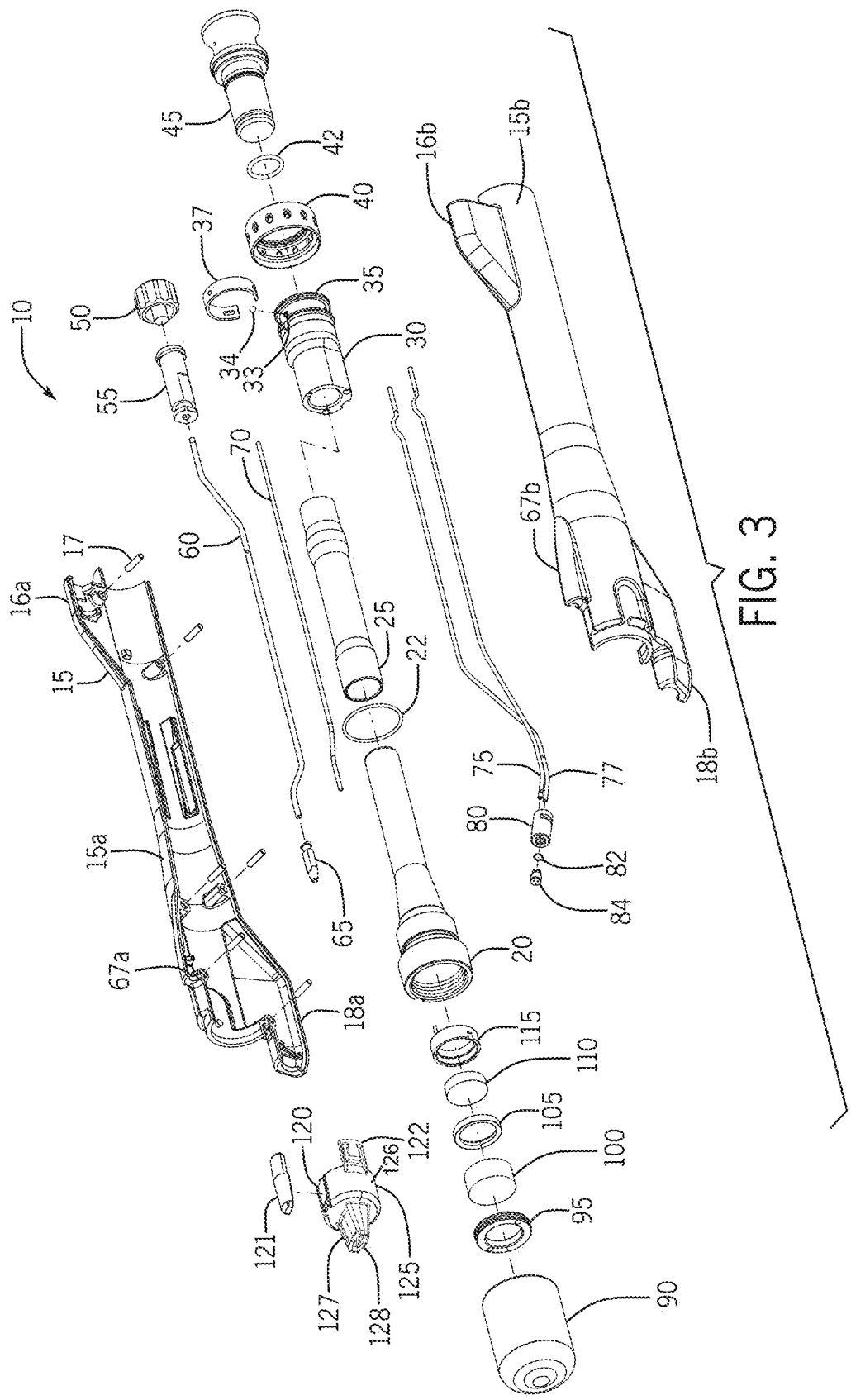
FIG. 3 illustrates an exploded assembly view of the handpiece assembly of FIG. 1 in accordance with some embodiments of the invention.

The optical housing 20 and other related components and structure of the handpiece assembly 10 can be seen in further detail in FIG. 3, showing an exploded assembly view of the handpiece assembly 10 of FIG. 1. In some embodiments of the invention, the optical housing 20 can house and support various optical components and support elements that can facilitate unobstructed and controlled delivery of laser energy through the housing 12 and out of the applicator 125. For example, in some embodiments, from the proximal end 11a towards the distal end 11b, the optical housing 20 can support and/or house an inner housing 115 coupled into the optical housing 20, an optical grating 110. Further, a spacer 105 can be positioned between the optical grating 110 and lens 100, and a nut 95 can secure the grating 110, spacer 105, and lens 100 to the distal end of the optical housing 20. Moving from the distal end of the optical housing 20 towards the proximal end 11b of the handpiece assembly 10, in some embodiments, the optical housing 20 can couple to a longitudinal extension 25. In some embodiments, the longitudinal extension 25 can extend towards the proximal end 11b of the handpiece assembly 10, and can be coupled with the cylinder 30 at one end, and plug 45 can coupled with the opposite cylinder end 35. In some embodiments of the invention, the proximal end of the cylinder adjacent the end 35 can include a spring 37 seated over a ball 34 positioned in ball seat 33. In some embodiments, various washers, seals, or other coupling elements or containment rings can be used to secure and/or seal one or more of the aforementioned components of the assembly 10. For example, some embodiments include O-ring 22 and/or O-ring 42 as shown.

In some embodiments of the invention, the handpiece assembly 10 can be coupled to an applicator that is disposable, and structured to be used with the handpiece assembly 10 once. For example, FIG. 7A illustrates an assembly view of a disposable applicator 225 in accordance with some embodiments of the invention, and FIG. 7B illustrates a front view of the disposable applicator 225 of FIG. 7A in accordance with some embodiments of the invention. In some embodiments, the applicator 225 can include a tip 227 extending from the tip body 226. In some embodiments, the tip 227 can include a tip end surface 227a that can be coupled to a patient's tissue, and applicator aperture 228 that can enable passage of laser energy, water, air (or other fluid), or a combination thereof. In some embodiments, during a treatment, laser radiation can pass through the optical housing and out of the aperture 228 with or without air or other fluid delivery from the delivery channel 230. Further, in some embodiments, either or both of the tubing 75, 77 can delivery fluid spray or mist and/or fluid to a region close to a target surface (e.g., such as bone, skin, dental tissue, or other biological surface) proximate the applicator 225.

In some embodiments, an air coupler housing 221 can extend from mating coupler 220 of the applicator body 226. In some embodiments, the air coupler housing 221 and applicator body 226 can be integral and structured to couple with the housing extension 67 and second body portion 13c of the handpiece assembly 10. In reference to FIG. 7C, illustrating a cross-section view through "A" of the disposable applicator tip of FIG. 7B, in some embodiments, the air coupler housing 221 can include the delivery channel 230 extending through at least a partial length of the air coupler housing 221 and coupled with tip channel 232, enabling fluid (e.g., such as air) to flow to the aperture 228. In some embodiments, to facilitate coupling of the connector 65 at the distal end 11a of the handpiece assembly 10 to the delivery channel 230 of the applicator body 226, the applicator body 226 can include a valve 250 (e.g., such as a duckbill valve) coupled to a seal 255. Thus, in some embodiments, when the disposable applicator 225 is coupled to the handpiece assembly 10, the connector can reversibly slide into the seal and couple to the valve 250. Further, as shown in FIGS. 7A and 7C, in some embodiments, the disposable applicator 225 can include a lens or window 245. In some embodiments, the window 245 can enable laser energy to travel out of the applicator body 226 and through the aperture 228 while maintaining a seal from the tip channel 232 and aperture 228.

In some embodiments, the applicator body 226 can be structured so that removal of the applicator from the handpiece assembly 10 causes at least a portion of the applicator break-away, rendering the applicator non-functional. FIG. 7D illustrates a cross-section view through "E" of the disposable applicator tip of FIG. 7B in accordance with some embodiments of the invention. In some embodiments, the applicator body 226 can include at least one applicator clip 222 that can couple to the mating form 140 of the handpiece assembly 10 with clip stop 142 being positioned at least partially through the clip 222 to secure the disposable applicator 225 to the second body portion 13c. As shown in FIG. 7D, and in close-up view of FIG. 7E, some embodiments include a notch 260 positioned at the edge 226a where the clip 222 extends away from the applicator body 226 and tip 227, and extending at least partially into the clip 222. In some embodiments, when the disposable applicator 225 is removed from the second body portion 13c of the handpiece assembly 10, the notch 260 can facilitate energy transfer through the clip 222 at the edge 226a so that the portion of the clip 222 extending away from the notch 260 breaksaway from the applicator body 226. In some embodiments, this serves to ensure or encourage the disposable applicator 226 is not reused with the handpiece assembly 10 because the disposable applicator 226 cannot be secured to the second body portion 13c of the handpiece assembly 10.

Figure 8:
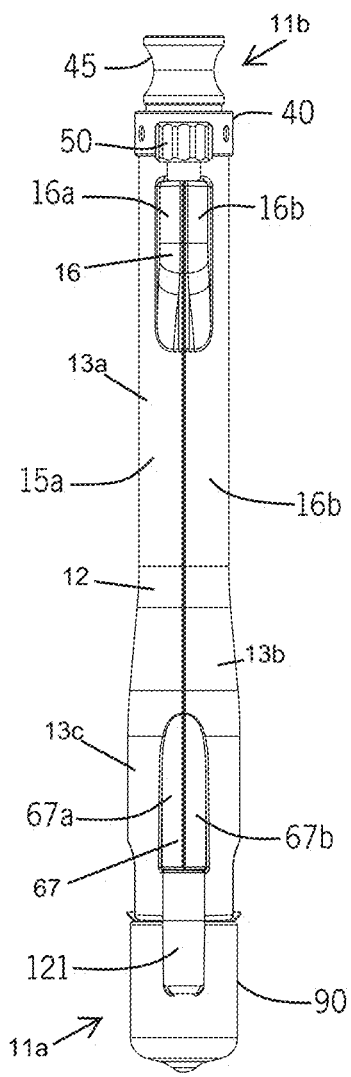
FIG. 8 illustrates a top view of the handpiece assembly of FIG. 1 in accordance some embodiments of the invention.
Figure 9:
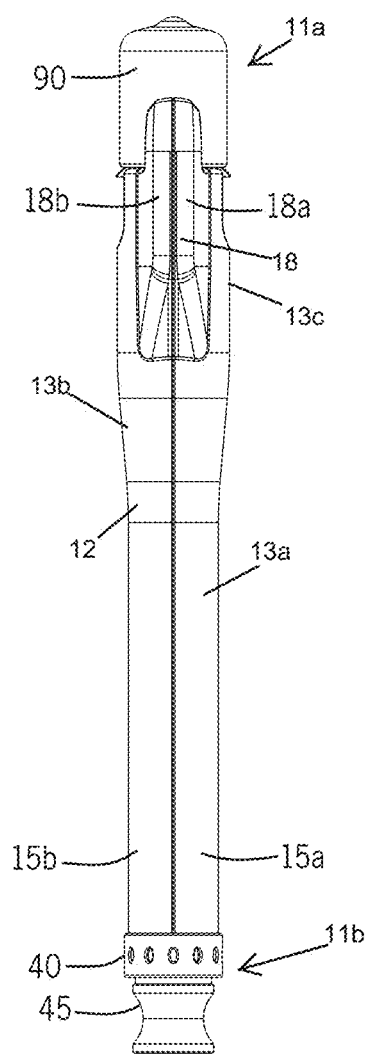
FIG. 9 illustrates a bottom view of the handpiece assembly of FIG. 1 in accordance some embodiments of the invention.
Figure 10:
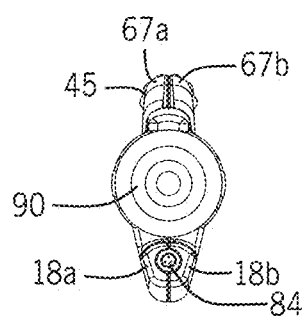
FIG. 10 illustrates a front distal end view of the handpiece assembly of FIG. 1 in accordance some embodiments of the invention.
Figure 11:
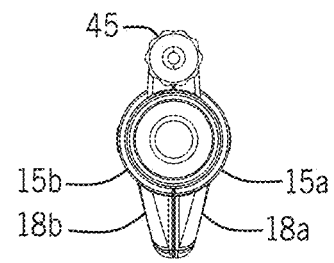
FIG. 11 illustrates a rear proximal end view of the handpiece assembly of FIG. 1 in accordance some embodiments of the invention.
Figure 12:
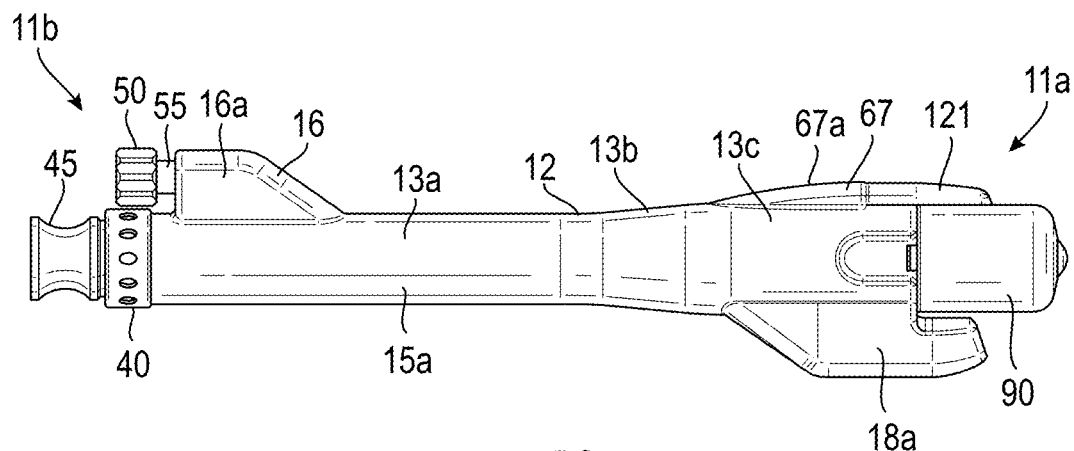
FIG. 12 illustrates a left-side view of the handpiece assembly of FIG. 1 in accordance some embodiments of the invention.
Figure 13:
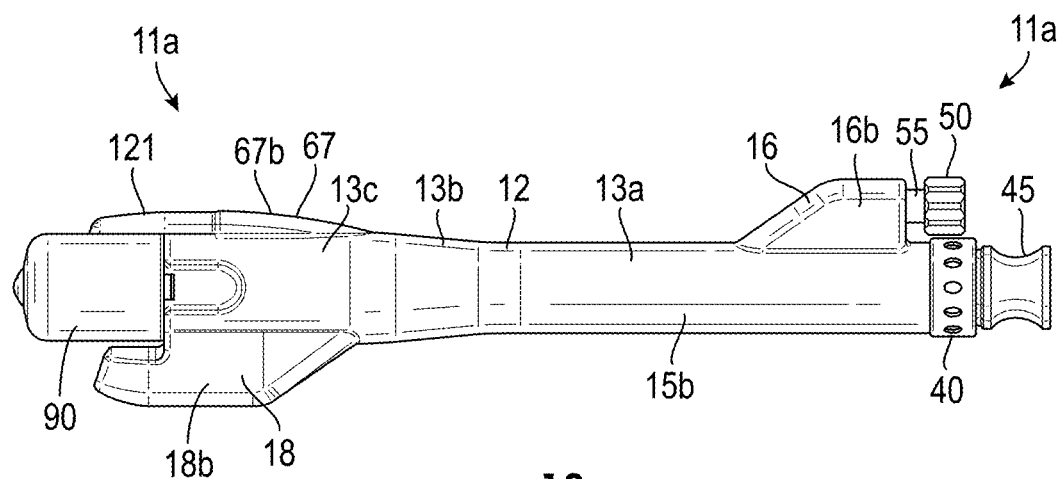
FIG. 13 illustrates a right-side view of the handpiece assembly of FIG. 1 in accordance some embodiments of the invention.

In some embodiments, the handpiece assembly 10 of FIG. 3 can include more or less O-rings, washers, seals, or other coupling elements or containment rings that can be used to secure and/or seal one or more of the aforementioned components of the assembly 10 without significantly changing or altering the operation and functional characteristics of the assembly 10. Various views of the handpiece assembly 10 are shown in further detail in FIGS. 8-13. For example, FIG. 8 illustrates a top view of the handpiece assembly 10 of FIG. 1, and FIG. 9 illustrates a bottom view of the handpiece assembly 10 of FIG. 1 in accordance some embodiments of the invention. Further, FIG. 10 illustrates a front distal end view of the handpiece assembly 10 of FIG. 1, and FIG. 11 illustrates a rear proximal end view of the handpiece assembly 10 of FIG. 1 in accordance with some embodiments of the invention. Further, FIG. 12 illustrates a left-side view of the handpiece assembly 10 of FIG. 1, and FIG. 13 illustrates a right-side view of the handpiece assembly 10 of FIG. 1 in accordance with some embodiments of the invention.

In some embodiments of the invention, the handpiece assembly 10 can be used to perform one or more medical, surgical, dental, or other health-related procedures using water spray, mist or vapor and/or air or other inert gas. In some embodiments, the water spray, mist or vapor and/or air or other inert gas can be used in combination with one or more laser pulses during the treatment. In some embodiments, the handpiece assembly 10 can include one or more supply lines and/or one or more delivery nozzles for air and/or water. In reference to exploded assembly view of FIG. 3, and FIG. 4 illustrating a cross-sectional view of the handpiece assembly 10, in some embodiments, the assembly 10 can include spray tubing 75 and/or water tubing 77. In some embodiments, the tubing 75, 77 can extend at least a partial length of the housing 12 extending from the proximal end 11b to the distal end 11a. In some embodiments, either or both tubes 75, 77 can couple into a spray mixer 84 with the tubes 75, 77 supported in a holder 80 and an O-ring 82 coupling the spray mixer 84 with the holder 80 positioned in the lower housing extension 18. Further, in some embodiments, the spray mixer 84 can be positioned at the distal end 11a on the side of the handpiece assembly 10 opposite or generally opposite the connector 65 and tubes 60, 70 for delivery of air or other fluid. In some embodiments, the air or other fluid delivery through one or more of the tubes 60, 70 can provide cooling and/or a positive pressure environment at a target or treatment site or area, and further, can remove debris from the area being lasered. Further, as shown in FIG. 4, in some embodiments, either or both tubes 75, 77 can extend through and be supported by at least a portion of the lower housing extension 18. In some embodiments, the spray mixer 84 can deliver air and water or other fluid. In some embodiments, the spray mixer 84 can deliver air and water or other fluid across a beam of electromagnetic energy emitted from the distal end 11a of the handpiece assembly 10. For example, in some embodiments, the lower housing extension 18 can curve inward so that the holder 80 positions the tubes 75, 77 pointing inward towards an axial center of the handpiece assembly. The effect of this can be seen in FIG. 14F.

In some embodiments, the assembly 10 can include tubing 60 and/or tubing 70. In some embodiments, the tubing 60, 70 can extend at least a partial length of the housing 12 extending from the proximal end 11b to the distal end 11a. In some embodiments, either or both tubing 60, 70 can couple into a connector 65 at the distal end 11a on one side of the handpiece assembly 10, and the connector 55 at the proximal end 11b of the handpiece assembly 10. Further, in some embodiments, the connector 55 can couple to the luer lock coupling 55. As shown in FIG. 4, in some embodiments, either or both tubes 60, 70 can extend through and be supported by at least a portion of the housing extension 67.

As described earlier, some embodiments the handpiece assembly 10 can include an applicator 125. In some embodiments, the applicator 125 can be used in close proximity to or in contact with a target tissue in preparation for and during treatment. In some embodiments, the handpiece assembly 10 can utilize one or more structural features to facilitate ergonomic packaging of supply lines and delivery nozzles for air and water and operation with a disposable applicator 125. In some embodiments, the applicator 125 is interchangeable. In some other embodiments, the applicator 125 can be disposable. In some embodiments, the applicator 125 can couple to the optical housing 20. In some embodiments of the invention, the optical housing 20 can facilitate delivery of laser energy through the housing 12 and out of the tip 125.

Figure 5A:
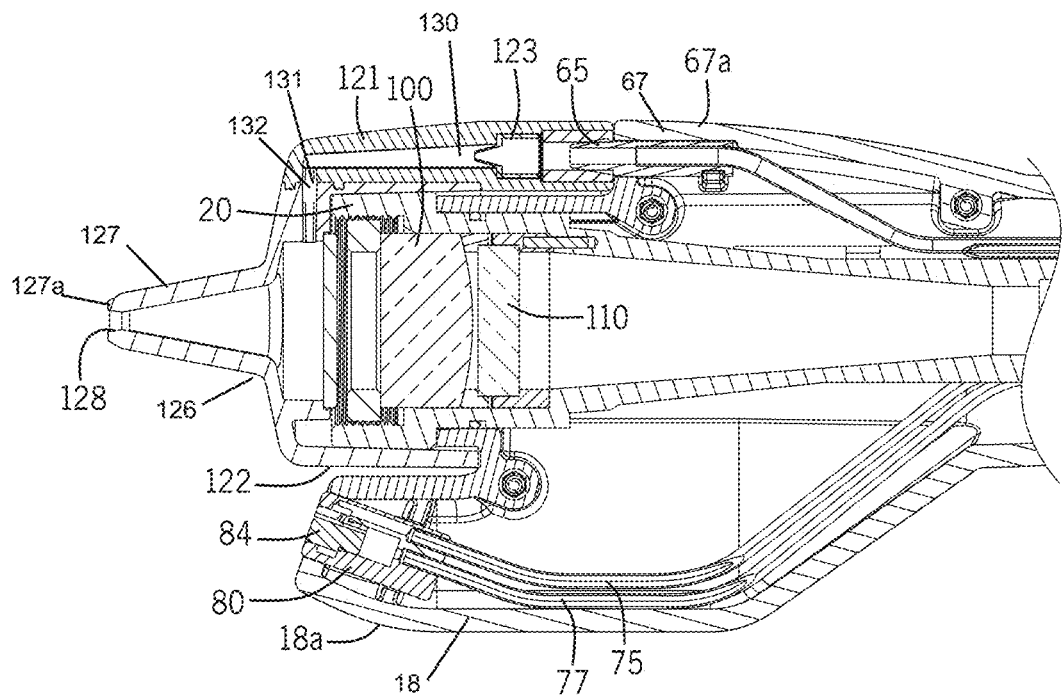
FIG. 5A illustrates a cross-sectional view of the distal end of the handpiece assembly of FIG. 1 in accordance some embodiments of the invention.
Figure 5B:
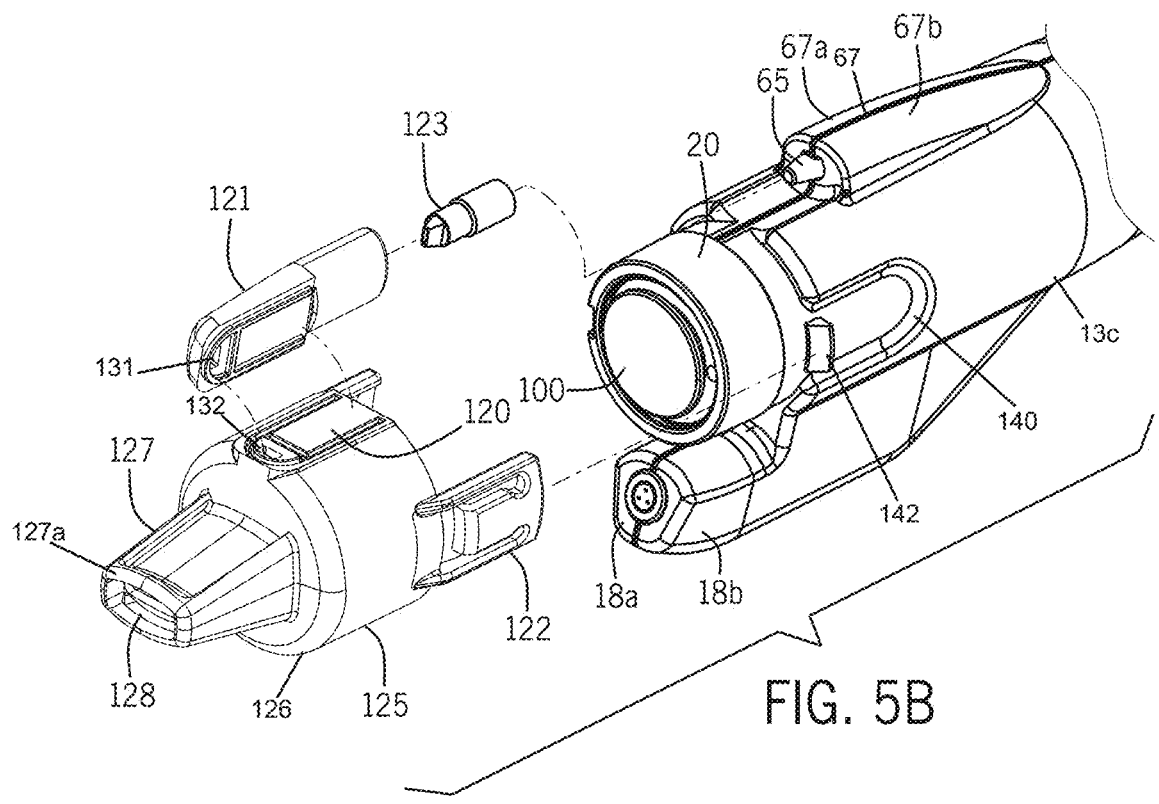
FIG. 5B illustrates an assembly view of the distal end of the handpiece assembly of FIG. 1 in accordance some embodiments of the invention.
Figure 6:
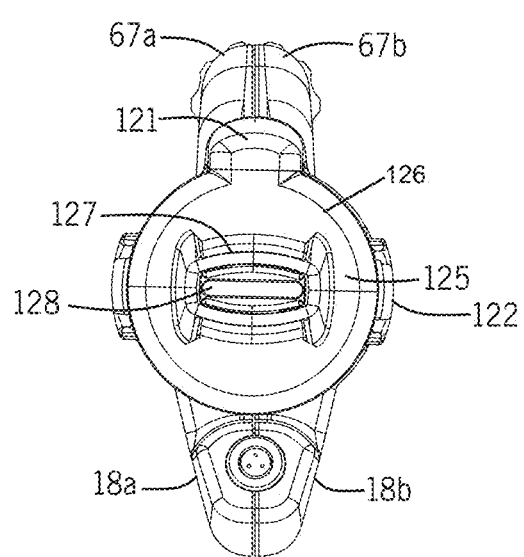
FIG. 6 illustrates a front view of the distal applicator tip positioned on the handpiece assembly of FIG. 1 in accordance some embodiments of the invention.
Figure 7:
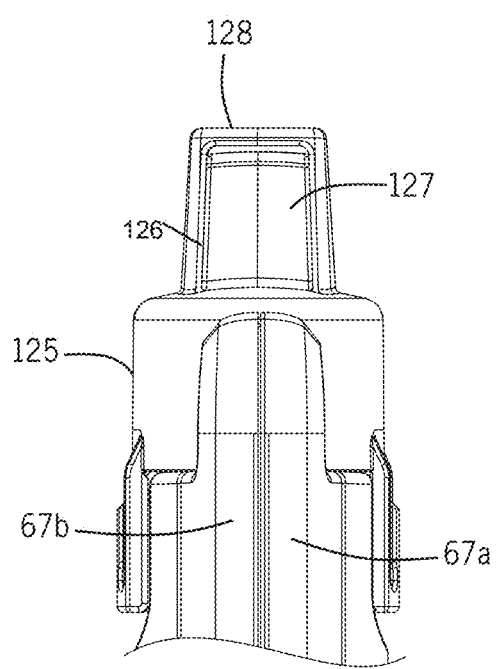
FIG. 7 illustrates a partial top view of the distal applicator tip positioned on the handpiece assembly of FIG. 1 in accordance some embodiments of the invention.

FIG. 5A illustrates a cross-sectional view of the distal end 11a of the handpiece assembly 10 of FIG. 1 in accordance with some embodiments of the invention, and FIG. 5B illustrates an assembly view of the distal end 11b of the handpiece assembly 10 of FIG. 1 in accordance with some embodiments of the invention. Further, FIG. 6 illustrates a front view of the distal applicator 125 positioned on the handpiece assembly 10 of FIG. 1 in accordance with some embodiments of the invention, and FIG. 7 illustrates a partial top view of the distal applicator 125 positioned on the handpiece assembly 10 of FIG. 1 in accordance with some embodiments of the invention. In some embodiments, a mating coupler 120 positioned on the applicator body 126 can couple with an air coupler housing 121. In some embodiments, the air coupler housing 121 and applicator body 126 can be integral (and thus is not an integral portion of the second body portion 13c). In some embodiments, the air coupler housing 121 can include a delivery channel 130 extending through at least a partial length of the air coupler housing 121 and coupled with a coupler orifice 131. In some embodiments, the housing 121 can couple to the mating coupler 120 of the applicator 125, and can further couple to the second body portion 13c of the housing 12, and further to the housing extension 67.

In some embodiments, the air coupler housing 121 and applicator body 126 can be integral (and thus is not an integral portion of the second body portion 13c). In some embodiments, the mating coupler 120 and air coupler housing 121 are integral, and the applicator 125 including the mating coupler 120 and air coupler housing 121 can couple to the second body portion 13c of the housing 12. As illustrated in FIGS. 5A and 5B, in some embodiments, the air coupler housing 121 can couple to air delivery connector 123, and at least one applicator clip 122 can couple to a mating form 140 with clip stop 142 being positioned at least partially through the clip 122 to secure the applicator 125 to the second body portion 13c of the housing. In some embodiments, the clip-stop 142 can be positioned and structured to be reversibly engaged with the applicator clip 122 to enable the applicator 125 to be attached and removed and replaced with another applicator 125. In some embodiments, any air or other cooling fluid source coupled to the auxiliary air input (luer lock coupling 50) can flow through tubing 60, 70, through the air deliver connector 123 to the delivery channel 130, and into the coupled tip channel 132 of the applicator 125 via coupler orifice 131.

In some embodiments of the invention, the handpiece assembly 10 can be used as a treatment device in contact mode (e.g., a portion of the handpiece assembly 10 can contact a portion of a patient during treatment). In some embodiments, the handpiece assembly 10 can include or couple to a disposable applicator 125 (attached to the distal end 11a of handpiece assembly 10) that is applied directly to the skin when the laser is fired. As shown in FIGS. 2-3, and 5A-5B, in some embodiments, the applicator 125 can include a tip 127 extending from the applicator body 126. In some embodiments, the tip 127 can include a tip end surface 127a that can be coupled to a patient's tissue, and applicator aperture 128 that can enable passage of laser energy, water, air (or other fluid), or a combination thereof. In some embodiments, during a treatment, laser radiation can pass through the optical housing and out of the aperture 128 with or without air or other fluid delivery from the delivery channel 130. Further, in some embodiments, either or both of the tubing 75, 77 can delivery fluid spray or mist and/or fluid to a region close to a target surface proximate the applicator 125.

In some embodiments, the dental laser can include a variety of different lasers, laser diodes, or other sources of light. In some embodiments of the invention, the handpiece can be utilized with a laser generating multiple microbeams in a single line per laser pulse. In some embodiments of the invention, the dental laser can include one or more erbium, chromium, yttrium, scandium, gallium garnet lasers (Er, Cr:YSGG). In some other embodiments, the laser sources of embodiments of the handpiece described herein can include an erbium, yttrium, aluminum garnet (Er:YAG) solid state laser; a chromium, thulium, erbium, yttrium, aluminum garnet (CTE:YAG) solid state laser; an erbium, yttrium orthoaluminate (Er:YAL03) solid state laser; a holmium, yttrium, aluminum garnet (Ho:YAG) solid state laser; a quadrupled neodymium, yttrium, aluminum garnet (quadrupled Nd:YAG) solid state laser; an excimer laser; or a carbon dioxide ($CO_2$) laser.

Some embodiments can use a combination of at least two laser wavelengths that can, in some embodiments, be implemented with a variety of different laser modules. In some embodiments, the use of two lasers outputting radiation at two different wavelengths can be used to achieve a synergistic effect. For example, in some embodiments, the radiation of a first wavelength is used to generate pressure waves within a fluid inside the root canal, and the pressure waves increase efficacy of a thermal disinfection that results from the application of radiation of a second wavelength. Thus, the radiation of the first wavelength prepares the area for the disinfection that occurs through using the radiation of the second wavelength.

In some embodiments, the electromagnetic energy source can be an erbium, chromium, yttrium, scandium, gallium garnet (Er, Cr:YSGG) solid state laser, which generates electromagnetic energy having a wavelength in a range of 2.70 to 2.80 microns. According to other embodiments of the invention, the electromagnetic energy source may be an erbium, yttrium, aluminum garnet (Er:YAG) solid state laser, which generates electromagnetic energy having a wavelength of 2.94 microns; chromium, thulium, erbium, yttrium, aluminum garnet (CTE:YAG) solid state laser, which generates electromagnetic energy having a wavelength of 2.69 microns; erbium, yttrium orthoaluminate (Er:YALO$_3$) solid state laser, which generates electromagnetic energy having a wavelength in a range of 2.71 to 2.86 microns; holmium, yttrium, aluminum garnet (Ho:YAG) solid state laser, which generates electromagnetic energy having a wavelength of 2.10 microns; quadrupled neodymium, yttrium, aluminum garnet (quadrupled Nd:YAG) solid state laser, which generates electromagnetic energy having a wavelength of 266 nanometers; argon fluoride (ArF) excimer laser, which generates electromagnetic energy having a wavelength of 193 nanometers; xenon chloride (XeCl) excimer laser, which generates electromagnetic energy having a wavelength of 308 nanometers; krypton fluoride (KrF) excimer laser, which generates electromagnetic energy having a wavelength of 248 nanometers; and carbon dioxide ($CO_2$), which generates electromagnetic energy having a wavelength in a range of 9 to 10.6 microns. In some embodiments, the electromagnetic energy can be generated using at least one laser diode. In some embodiments, the laser that includes a laser diode that generates electromagnetic energy having a wavelength that ranges from about 405 nm to about 1320 nm.

In some embodiments of the invention, the total laser power output of the handpiece can be up to about 9 Watts at about 15 Hz. In some embodiments of the invention, the total energy per pulse can be set between 10 mJ and 600 mJ. In some embodiments of the invention, the energy per spot from the handpiece can be 10 mJ to 60 mJ. In some embodiments, the spot diameter can be between 200 um and 600 um. In some embodiments, the energy per spot can be 10 J/cm$^2$ to 200 J/cm$^2$. In some embodiments, the depth of one hole can be up to 1 mm. In some embodiments, the surface coverage can be 5% to 50%. In addition, the range of power in another embodiment can now go to 16 watts at 15 hz, 1,000 mJ, and energy per spot up to 100 mJ.

Figure 14B:
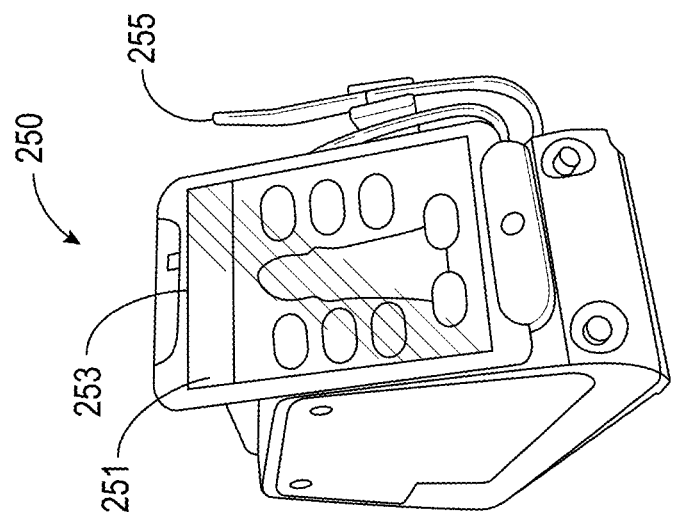
FIGS. 14A-14B show example dental laser stations in accordance with some embodiments of the invention.
Figure 14A:
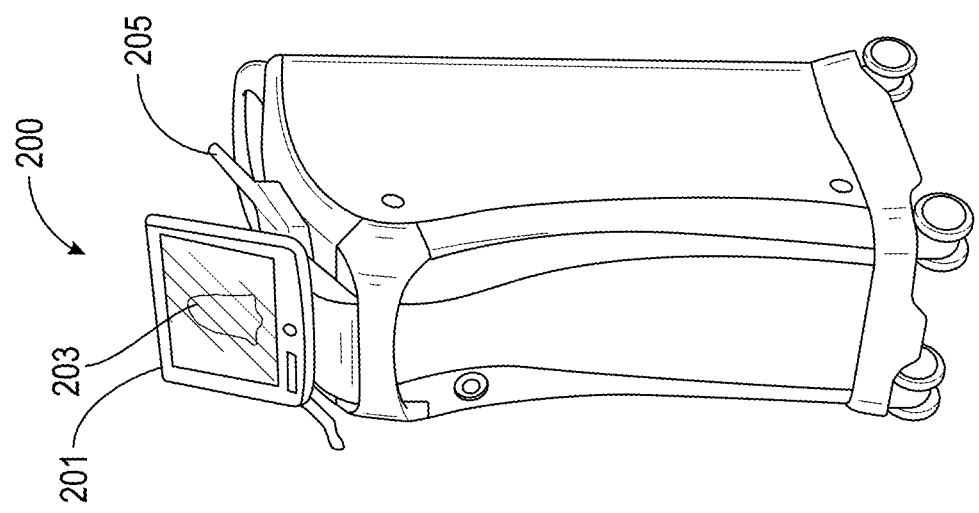

Some non-limiting embodiments of the invention can include the handpiece assembly 10 being a handpiece 205 of the dental laser station 200 shown in FIG. 14A. In other embodiments, the handpiece assembly 10 can be a handpiece 255 of the dental laser station 250 shown in FIG. 14B. In some embodiments of the invention, the handpiece assembly 10 can form part of a dental laser system that includes a display. In some embodiments, the display can comprise a touchscreen display configured to enable a user to interact with a graphical user interface (hereafter "GUI"). In some embodiments, user interactions with the GUI can include using single, multiple, or repeated physical contact with the display to initiate one or more functions of the dental laser system and a coupled handpiece. For example, in some embodiments, the display can include a GUI comprising one or more displayed menus that can be navigated by user to control or monitor one or more functions of the handpiece assembly 10. For example, some non-limiting embodiments include of dental laser station 200 includes display 201 including a GUI 203, and another non-limiting example embodiments includes dental laser station 250 with display 251 including a GUI 253.

As described earlier, some embodiments the handpiece assembly 10 can include an applicator 125, 225. In some embodiments, the applicator 125, 225 can be used in close proximity to, or in contact with, a target tissue in preparation for and during treatment. Further, in some embodiments, the handpiece assembly 10 can utilize one or more structural features to facilitate ergonomic packaging of supply lines and delivery nozzles for air and water and operation with a disposable applicator 125, 225, thus ensuring the operator can maneuver the handpiece assembly 10 on or over a treatment area of a patient without the risk of unintentional dragging or snagging of supply lines and delivery nozzles.

Figure 14C:
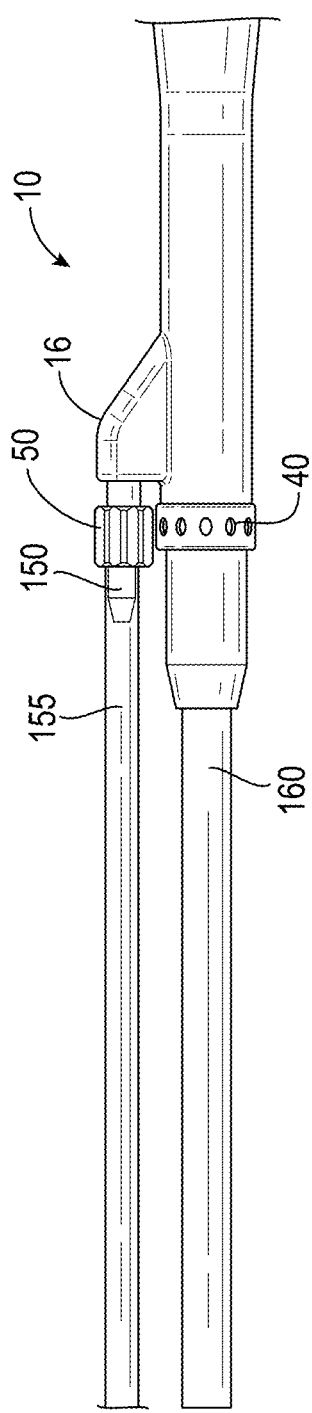
FIG. 14C illustrates a handpiece assembly with a coupled fiber optic cable in accordance some embodiments of the invention.
Figure 14D:
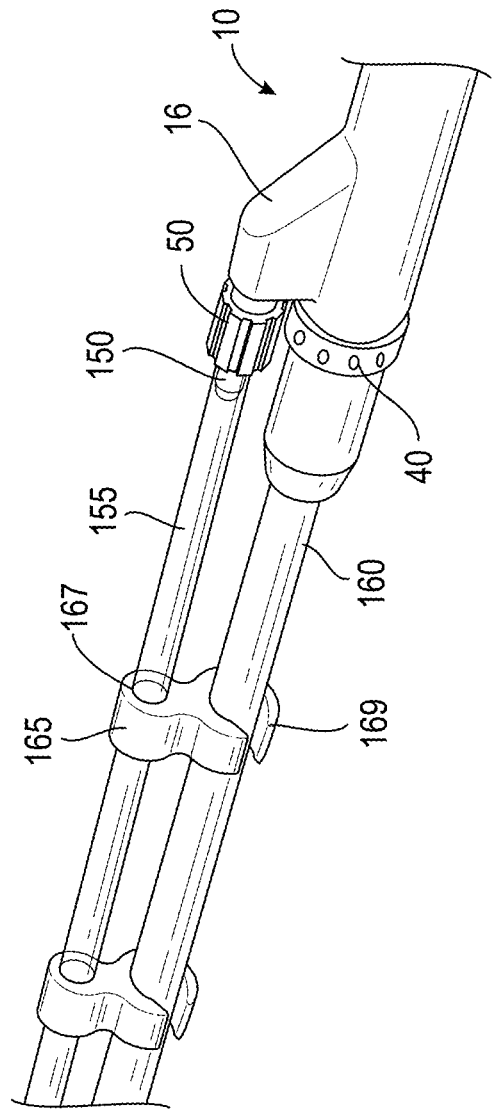
FIG. 14D illustrates a handpiece assembly with a fiber optic cable and coupled air supply tube in accordance some embodiments of the invention.

In some embodiments, the handpiece assembly 10 (e.g., such as handpiece 205 and/or handpiece 255) can be configured to receive laser energy by coupling to a fiber optic cable that can be coupled to a source of electromagnetic energy. For example, FIG. 14C illustrates a handpiece assembly with a fiber optic cable 160 in accordance some embodiments of the invention. Further, in some embodiments of the invention, the upper housing extension 16 can can enable reversible coupling of a fluid input, where the upper housing extension 16 can include a luer lock coupling 50 that can enable the coupling of the handpiece assembly 10 to an auxiliary air input tube 155. In some embodiments, the auxiliary air supply tube 155 and fiber optic cable 160 can be coupled to enable convenient and/or safe handling and management of the fiber optic cable 160 and/or the auxiliary air supply tube 155. For example, FIG. 14D illustrates a handpiece assembly with a coupled fiber cable 160 and coupled air supply tube 155 in accordance some embodiments of the invention. As illustrated, some embodiments include a coupler 165 comprising an aperture 167 supporting the air supply tube 155, and aperture 169 supporting the fiber optic cable 160.

Figure 14F:
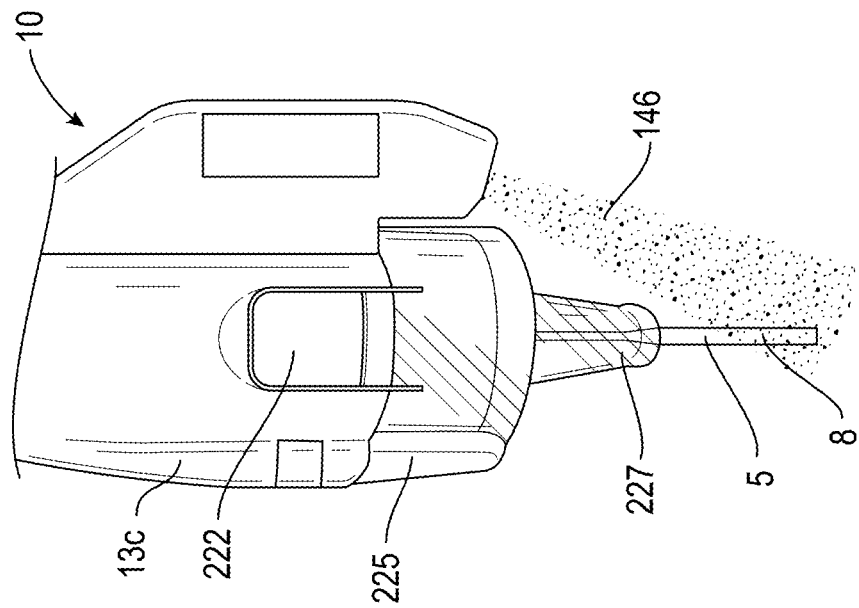
FIG. 14F illustrates a beam and spray of the handpiece assembly in accordance some embodiments of the invention.
Figure 14E:
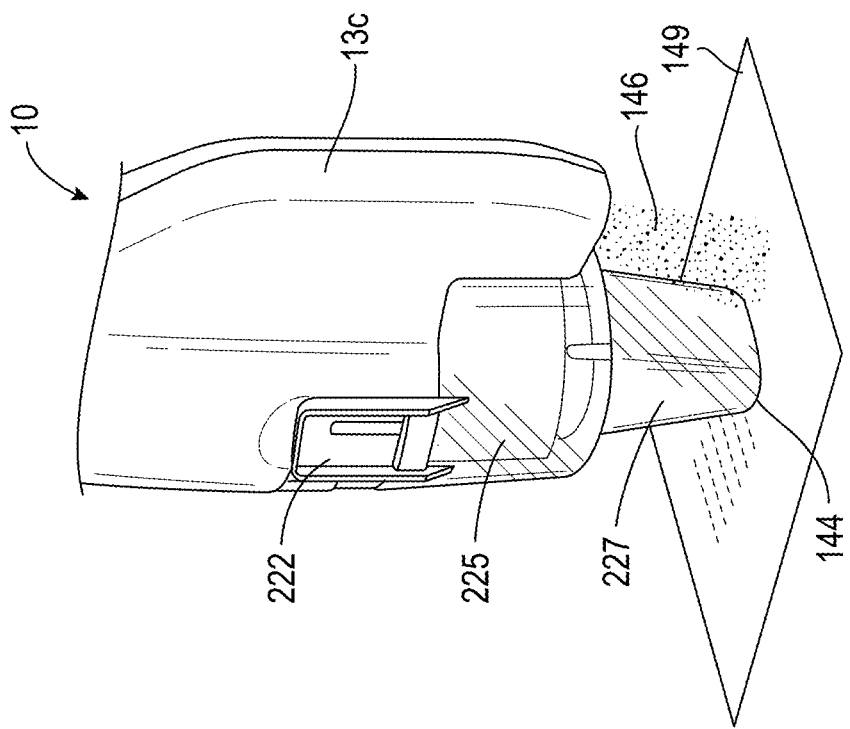
FIG. 14E illustrates the handpiece assembly in operation in contact mode in accordance some embodiments of the invention.

FIG. 14E illustrates one example embodiments of the handpiece assembly 10 in operation in contact mode in accordance some embodiments of the invention. As shown, in some embodiments, tip 227 can be coupled with a patience tissue surface 149 at an interface 144 where spray 146 can be directed. FIG. 14F illustrates a beam 5 and spray 146 of the handpiece assembly in accordance some embodiments of the invention. In some embodiments, the spray 146 can intersect with the beam 5 (shown as region 8). As discussed earlier, in some embodiments, the lower housing extension 18 can curve inward so that the holder 80 positions the tubes 75, 77 pointing inward towards an axial center of the handpiece assembly, and allowing the spray mixer 84 to deliver air and water or other fluid across a beam 5.

Referring back to FIGS. 14A and 14B, in some embodiments of the invention, the handpiece assembly 10 can form part of a dental laser system or station 200, 250 that includes a display. For example, some non-limiting embodiments include of dental laser station 200 that includes display 201, and another non-limiting example embodiment includes dental laser station 250 with display 251. In some embodiments, the display 201, 251 can comprise a touchscreen display configured to enable a user to interact with a graphical user interface (hereafter "GUI"). For example, some non-limiting embodiments includes display 201 including a GUI 203, and another non-limiting example embodiment includes display 251 including a GUI 253. In some embodiments, user interactions with the GUI 203, 251 can include using single, multiple, or repeated physical contact with the display 201, 251 to initiate one or more functions of the dental laser system and a coupled handpiece (e.g., such as handpiece assembly 10). For example, in some embodiments, the display 201, 251 can include a GUI 203, 253 comprising one or more displayed menus that can be navigated by user to control or monitor one or more functions of the handpiece assembly 10.

Figure 15:
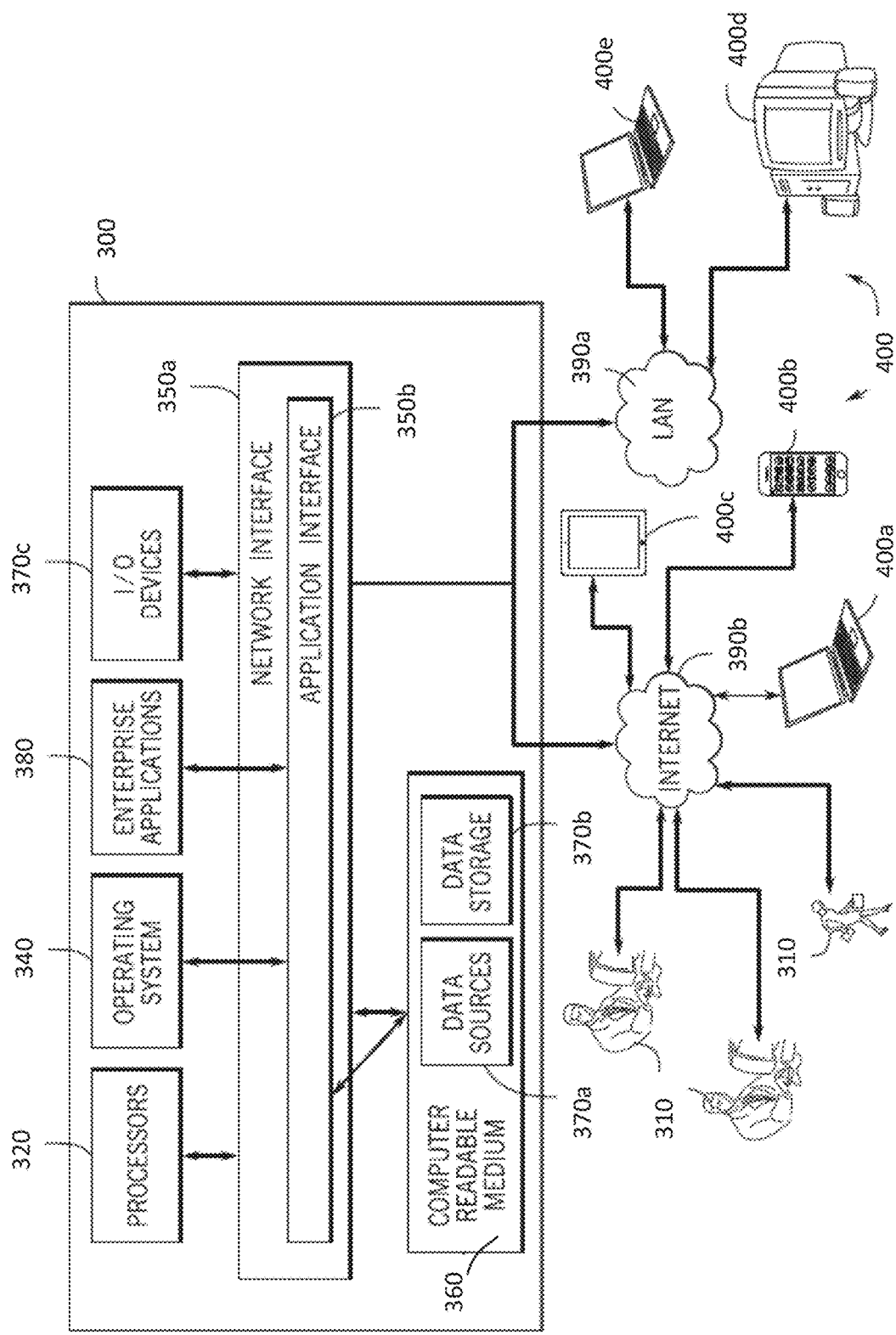
FIG. 15 illustrates a computer system useful for controlling, monitoring, and/or networking to a dental laser station controlling a handpiece assembly of FIG. 1 in accordance with some embodiments of the invention in accordance some embodiments of the invention.

In some embodiments, the display (e.g., such as display 201 or display 251) can form a communication of a computer system of the dental laser station (which can include a removable conventional tablet computer including a tablet display capable of displaying the GUI and/or a coupled remote and/or internet and/or cloud-based computer system). For example, FIG. 15 illustrates a computer system 300 useful for controlling and/or networking to a handpiece assembly 10 of a dental laser station in accordance with some embodiments of the invention. In some embodiments, the system 300 can control one or more components or systems of a dental laser station (e.g., such as the dental laser station 200 or dental laser station 250) including any operation portion of a remote access function of the dental laser station 200, 250. In some embodiments, the dental laser station 200 and/or dental laser station 250 can comprise the system 300. In some embodiments of the invention, control systems, displays, and associated GUIs can be used to control and/or monitor some aspect, function, or operational characteristic of a dental laser station (e.g., such as the dental laser station 200 or dental laser station 250) and/or a coupled component (e.g., such as handpiece assembly 10), and/or communicate some function or operational characteristic, including one or more control and/or operating parameters of the handpiece assembly 10.

In some embodiments of the invention, the system 300 can comprise operating and processing modules for the handpiece assembly 10. In some embodiments, the system 300 can include at least one computing device including one or more processors 320. Some processors 320 can include processors residing in one or more conventional server platforms including within a cloud of computing resources. In some embodiments, the system 300 can include a network interface 350a and/or an application interface 350b coupled to at least one processor 320 capable of running at least one operating system 340. Further, in some embodiments, the at least one processor 320 can be capable of running one or more of the software modules (e.g., such as enterprise applications 380). In some embodiments, the system 300 can comprise at least one computer readable medium 360 coupled to at least one data storage device 370b, and/or at least one data source 370a, and/or at least one input/output device 370c. In some embodiments, the computer readable medium 360 can be any data storage device that can store data, which can thereafter be read by a computer system (such as the system 300). Examples of the computer readable medium 360 can include hard drives, network attached storage (NAS), read-only memory, random-access memory, FLASH based memory, CD-ROMs, CD-Rs, CD-RWs, DVDs, magnetic tapes, other optical and non-optical data storage devices, or any other physical or material medium which can be used to tangibly store the desired information or data or instructions and which can be accessed by a computer or processor (including processors 320).

Some embodiments include a remote access system and method embodied as computer readable code on the computer readable medium 360. In some embodiments of the invention, the computer readable medium 360 can also be distributed over a conventional computer network via the network interface 350a so that the computer readable code can be stored and executed in a distributed fashion. For example, in some embodiments, one or more components of the system 300 can be tethered to send and/or receive data through a local area network ("LAN") 390a. In some embodiments, one or more components of the system 300 can be tethered to send or receive data through an internet 390b (e.g., a wireless internet). Further, in some embodiments, at least one software application 380 running on one or more processors 320 can be configured to be coupled for communication over a network 390a, 390b. In some embodiments, one or more components of the network 390a, 390b can include one or more resources for data storage, including any other form of computer readable media beyond the media 360 for storing information and including any form of computer readable media for communicating information from one electronic device to another electronic device.

In some embodiments, the network 390a, 390b can include wide area networks ("WAN"), direct connections (e.g., through a universal serial bus port) or other forms of computer-readable media 360, or any combination thereof. Further, in some embodiments, one or more components of the network 390a, 390b can include a number of client devices which can be one or more display and/or computers 400 including for example desktop computers 400d, laptop computers 400a, 400e, digital assistants and/or personal digital assistants and/or digital tablets (shown as 400c), cellular phones or mobile phones or smart phones (shown as 400b), pagers, internet appliances, and other processor-based devices. In general, a client device can be any type of external or internal devices such as a conventional mouse, CD-ROM, DVD, keyboard (e.g., implemented as a hardware keyboard and/or a software-displayed keyboard, a passive or active display, or other input or output devices 370c. In some embodiments, various other forms of computer-readable media 360 can transmit or carry instructions to one or more computers 400, including a router, private or public network, or other transmission device or channel, both wired and wireless. In some embodiments, the software modules 380 can be configured to send and receive data from a database (e.g., from a computer readable medium 360 including data sources 370a and data storage 370b that can comprise a database), and data can be received by the software modules 380 from at least one other source.

In some embodiments, at least one of the software modules 380 can be configured within the system 300 to output data to at least one user 310 via at least one digital display (e.g., to a computer comprising a digital display). In some embodiments, the display can include the display 201 or display 251 shown in FIGS. 14A and 14B respectively. In some embodiments, any of the computers 400 can comprise the display 201, 251. In some embodiments, the system 300 as described can enable one or more users 310 to receive, analyze, input, modify, create and send data to and from the system 300, including to and from one or more enterprise applications 380 running on the system 300. Some embodiments include at least one user 310 coupled to a computer 400 accessing one or more modules of the dentistry control system including at least one enterprise applications 380 via a stationary I/O device 370c through a LAN 390a. In some other embodiments, the system 300 can enable at least one user 310 (through computer 400) accessing enterprise applications 380 via a stationary or mobile I/O device 370c through an internet 390a. In some embodiments, the software modules 380 can include a server-based software platform that can include dentistry control software modules suitable for hosting at least one user 310 account and/or at least one patient account or record.

In some embodiments, the GUI can display one or more selectable menus, messages, and/or icons that can be used to select a dental handpiece and/or control at least one function of the handpiece such as handpiece assembly 10. In some embodiments, basic settings can include pre-set settings, minimum and maximum settings. In some embodiments, the settings can include energy, pulse rate, and power settings of the laser. Other settings can include air and water flow rate settings. Further, in some embodiments, the specific settings shown can vary based and are shown as non-limiting embodiments only. Other settings can be used without departing from the invention as described herein. For example, in some embodiments, displayed menus can include category buttons, any one of which can have one or more control system attributes. In some embodiments, these category buttons may be defined as, but not be limited to, dentin, enamel, anterior deciduous, hemostasis, perio, endo, incision/excision, de-sensitization and osseous.

In some embodiments, the display 300 can comprise "soft" buttons that can be graphically rendered in a GUI, and/or can be hard buttons adjacent to the displays on a dental tool or associated control equipment, and/or a remote control or a WiFi linked system. In some embodiments, using one or more portions of the GUI, a user can enter, select, and/or modify one or more system or operational variables or attributes. For example, using at least one displayed feature, a user can use the GUI to control a plurality of system or operational variables or attributes. In some embodiments, these parameters can be modified interactively to adjust and optimize the operational characteristics of a dental laser prior to starting a dental procedure, during a dental procedure, and/or after a dental procedure has been performed. Some non-limiting example embodiments of GUI's configured to display one or more selectable menus, messages, and/or icons that can be used to select a dental handpiece and/or control at least one function of the handpiece assembly 10 are shown un FIGS. 16 and 17.

Figure 16:
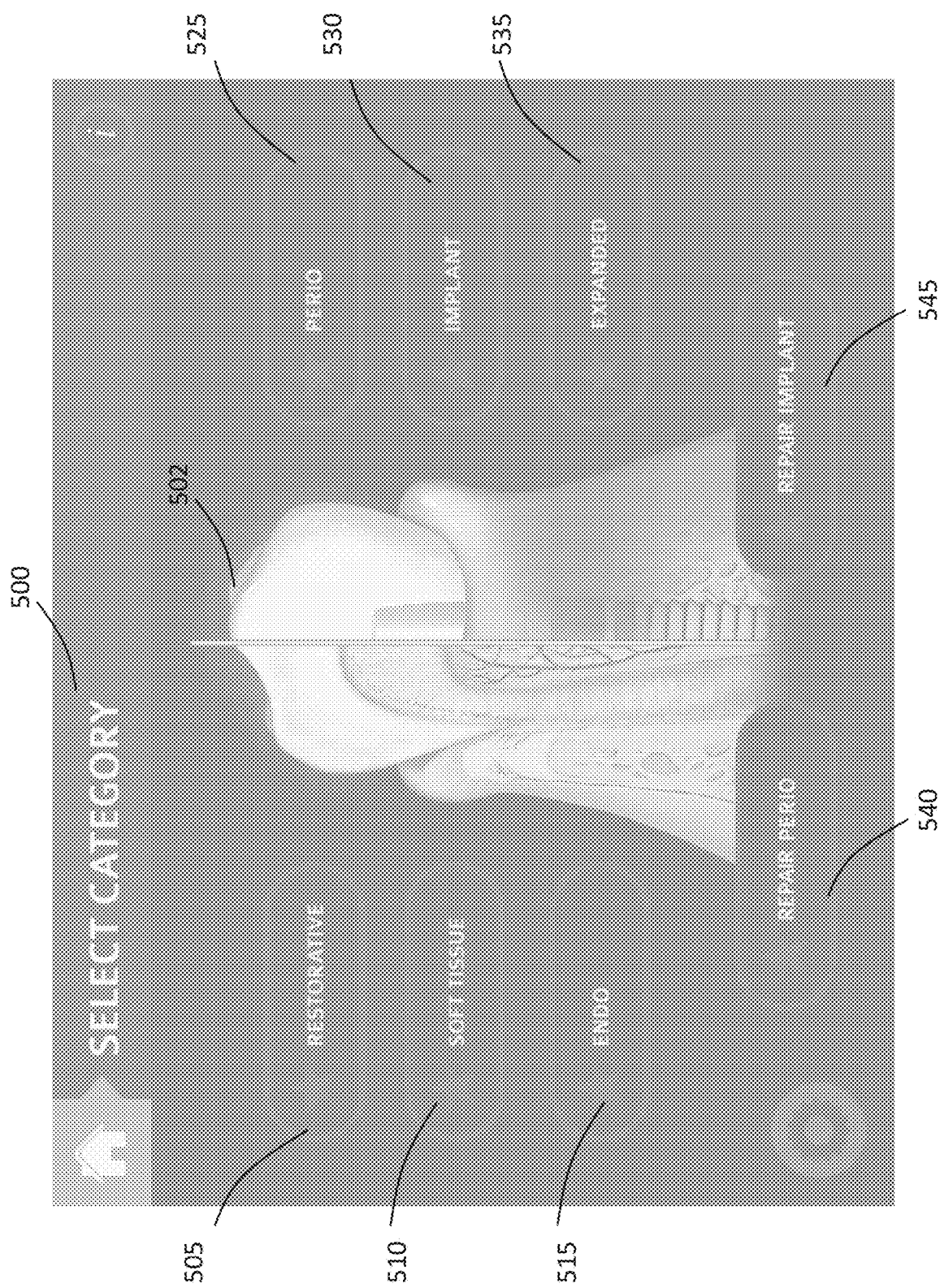
FIGS. 16-17, and 17A illustrate example GUI displays configured for showing operational and control parameters of the handpiece assembly.

In reference to FIG. 16, some embodiments include a select category 500 menu with system settings and parameters for various selectable procedures that can be performed using the handpiece assembly 10. Some embodiments include system settings and parameters for soft tissue procedures, options, and steps (shown as selectable icon 505). Some further embodiments include system settings and parameters for restorative procedures, options, and steps (shown as selectable icon 510). Other embodiments include system settings and parameters for endodontic procedures, options, and steps (shown as selectable icon 515). Some further embodiments include system settings and parameters for periodontic procedures, options, and steps (shown as selectable icon 525). Some embodiments of the invention include system settings and parameters for implant procedures, options, and steps (shown as selectable icon 530). Some further embodiments include system settings and parameters for expanded procedures, options, and steps (shown as selectable icon 535). Some further embodiments include system settings and parameters for repair periodontic procedures, options, and steps (shown as selectable icon 530). Further embodiments include system settings and parameters for repair implant procedures, options, and steps (shown as selectable icon 530).

Figure 17:
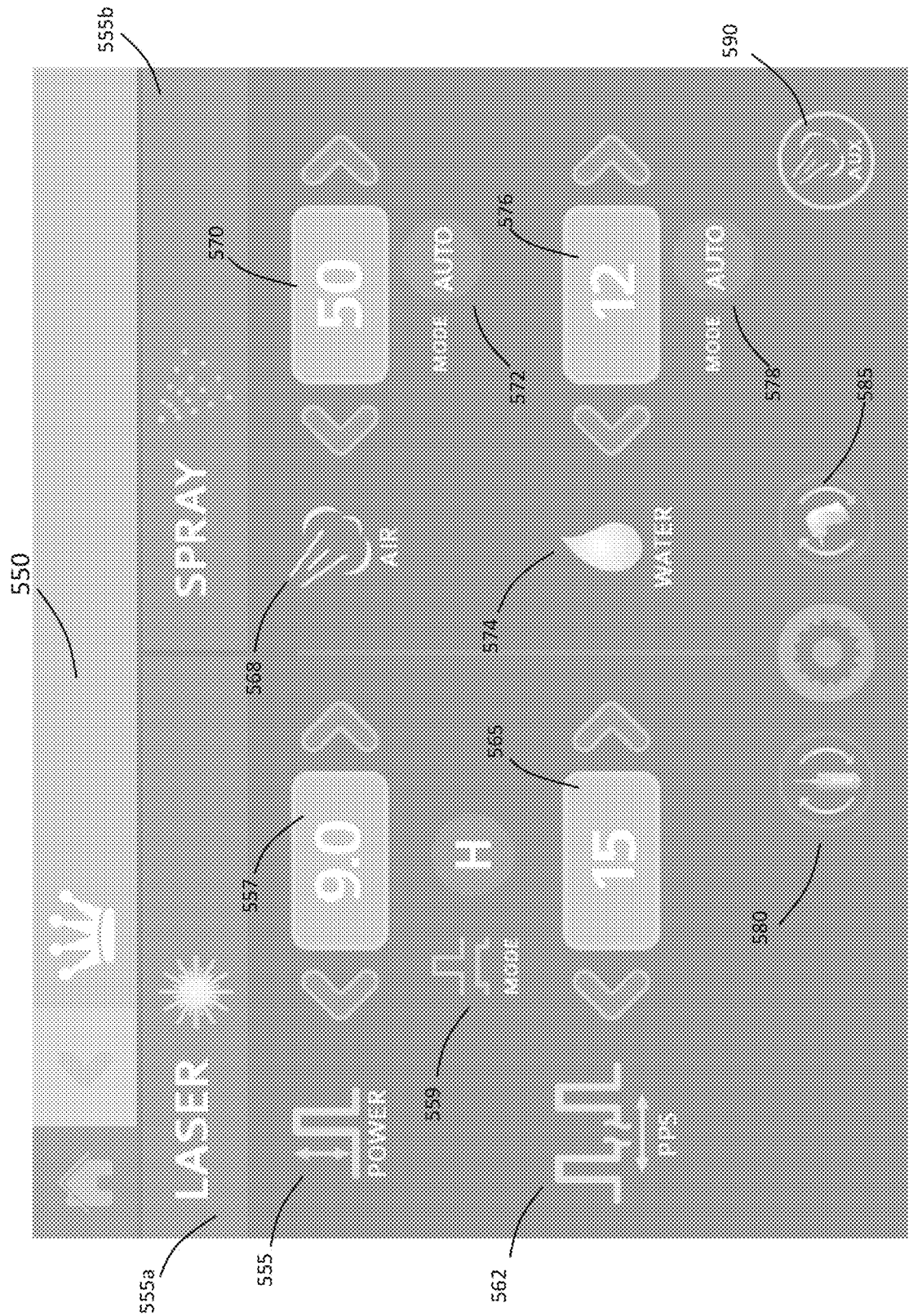

In reference to FIG. 17, some embodiments include a GUI 550 configured for showing operational and control parameters of the handpiece assembly 10. For example, some embodiments include a laser parameter display 555a for displaying and/or controlling laser parameters of the handpiece assembly 10. Other embodiments include a spray parameter display 555b for displaying and/or controlling spray parameters of the handpiece assembly 10. Some embodiments include a power meter 555 with selectable power level 557, and a laser mode 559 display and/or selector. In some embodiments, a selectable slider for modifying and/or setting at least one parameter of the procedure can be displayed. Some further embodiments include a pulse display 562 with selectable pulse icon 565. In some embodiments, the GUI 550 can include an air delivery display 568 with air setting 570 and/or air mode 572. Further, some embodiments include a water delivery display 574 with water setting 576, and water mode icon 578. Some embodiments also include an auxiliary icon 590 for selecting or indicating auxiliary components and/or sources providing air and/or water. In some embodiments, a handpiece exchange icon 580 and/or tip exchange icon 585 can be used to install and/or swap a handpiece and/or tip of the handpiece assembly 10.

Figure 17A:
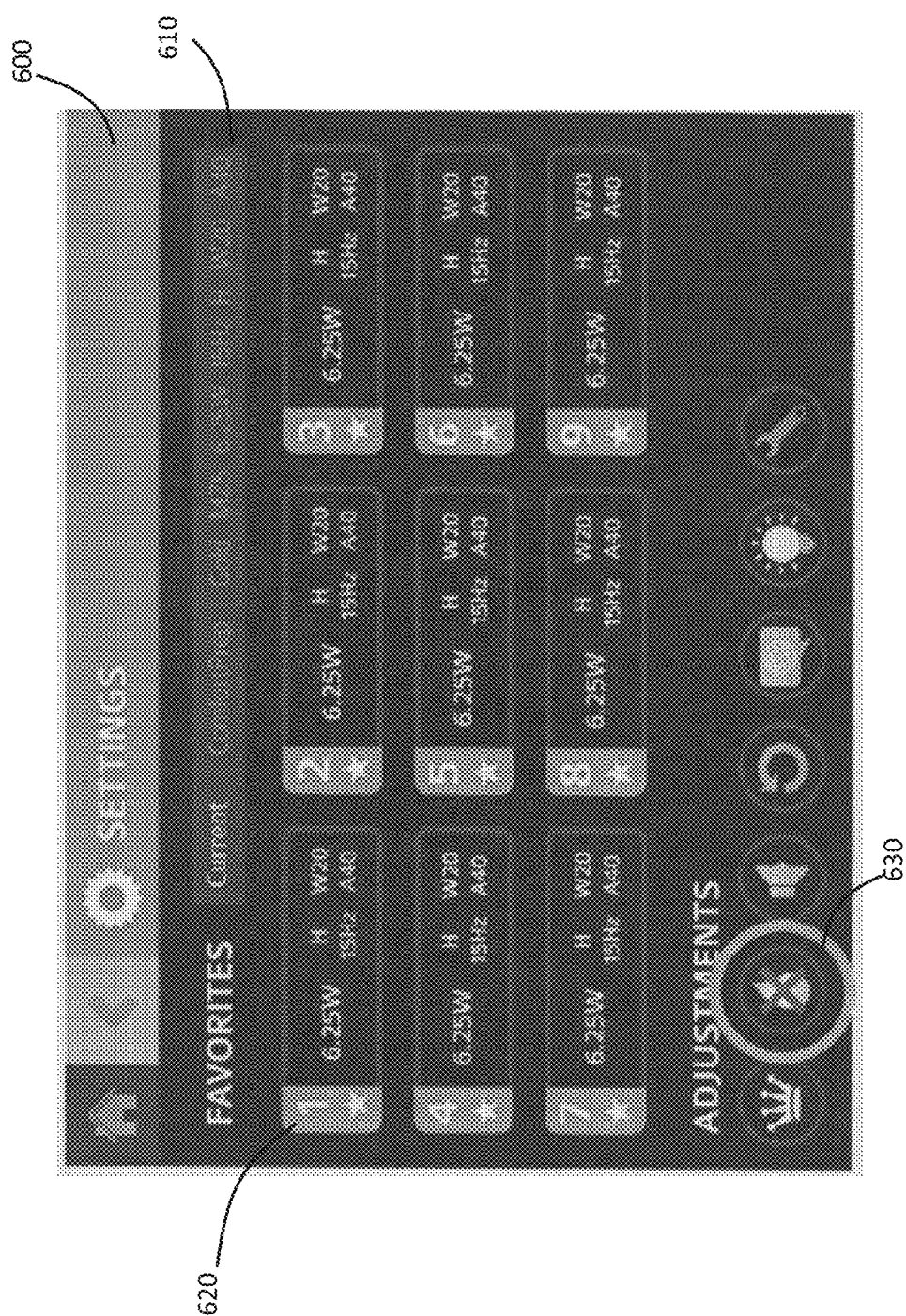

In reference to FIG. 17A, illustrating another example GUI display configured for showing operational and control parameters of the handpiece assembly 10, some embodiments include a GUI 600 comprising selectable favorite settings. In some embodiments, the GUI 600 can include a current setting display bar 610 displaying or monitoring one or more operating parameters or settings of the handpiece assembly 10 and/or a coupled laser system (e.g., such as dental laser station 200 and/or dental laser station 250). In some embodiments, a user can select one or more settings, operational parameters and/or monitored parameters of the handpiece assembly 10 and/or a coupled laser system (e.g., such as dental laser station 200 and/or dental laser station 250 by accessing one or more favorite icons 620.

With the above embodiments in mind, it should be understood that the invention can employ various computer-implemented operations involving dentistry control data stored in computer systems. Moreover, the above-described databases and models throughout the dentistry control can store analytical models and other data on computer-readable storage media within the system 300 and on computer-readable storage media coupled to the system 300. In addition, the above-described applications of the dentistry control system can be stored on computer-readable storage media within the system 300 and on computer-readable storage media coupled to the system 300. These operations are those requiring physical manipulation of physical quantities. Usually, though not necessarily, these quantities take the form of electrical, electromagnetic, or magnetic signals, optical or magneto-optical form capable of being stored, transferred, combined, compared and otherwise manipulated.

Any of the operations described herein that form part of the invention are useful machine operations. The invention also relates to a device or an apparatus for performing these operations. The apparatus can be specially constructed for the required purpose, such as a special purpose computer. When defined as a special purpose computer, the computer can also perform other processing, program execution or routines that are not part of the special purpose, while still being capable of operating for the special purpose. Alternatively, the operations can be processed by a general purpose computer selectively activated or configured by one or more computer programs stored in the computer memory, cache, or obtained over a network. When data is obtained over a network the data can be processed by other computers on the network, e.g. a cloud of computing resources.

The embodiments of the present invention can also be defined as a machine that transforms data from one state to another state. The data can represent an article, that can be represented as an electronic signal and electronically manipulate data. The transformed data can, in some cases, be visually depicted on a display, representing the physical object that results from the transformation of data. The transformed data can be saved to storage generally or in particular formats that enable the construction or depiction of a physical and tangible object. In some embodiments, the manipulation can be performed by a processor. In such an example, the processor thus transforms the data from one thing to another. Still further, the methods can be processed by one or more machines or processors that can be connected over a network. Each machine can transform data from one state or thing to another, and can also process data, save data to storage, transmit data over a network, display the result, or communicate the result to another machine. Computer-readable storage media, as used herein, refers to physical or tangible storage (as opposed to signals) and includes without limitation volatile and non-volatile, removable and non-removable storage media implemented in any method or technology for the tangible storage of information such as computer-readable instructions, data structures, program modules or other data.

Although method operations can be described in a specific order, it should be understood that other housekeeping operations can be performed in between operations, or operations can be adjusted so that they occur at slightly different times, or can be distributed in a system which allows the occurrence of the processing operations at various intervals associated with the processing, as long as the processing of the overlay operations are performed in the desired way.

It will be appreciated by those skilled in the art that while the invention has been described above in connection with particular embodiments and examples, the invention is not necessarily so limited, and that numerous other embodiments, examples, uses, modifications and departures from the embodiments, examples and uses are intended to be encompassed therein. Various features and advantages of the invention are set forth in the following claims.

The invention claimed is:

1. A system comprising;
   a laser delivery system configured to deliver electromagnetic energy via a fiber optic cable; and
   a handpiece assembly coupled to the fiber optic cable and configured to receive the electromagnetic energy from the laser delivery system, the handpiece assembly further configured to receive an air supply and at least one fluid, and to selectively, simultaneously deliver the electromagnetic energy, air supply and the at least one fluid to a target surface, the handpiece assembly comprising components including:
      a spray mixer positioned at a distal end of the handpiece assembly, the spray mixer coupled to fluid lines of the plurality of fluid lines; and
      an air coupler comprising an air input port and an air delivery channel, the air coupler coupled to a housing extension of the handpiece assembly, the air coupler configured to couple on-demand air to the handpiece assembly via the air input port and air delivery channel, the air delivery channel configured to deliver the air supply from the air input port to the target surface via a tip of an exchangeable disposable, single use applicator that is coupled to a distal end of the handpiece assembly and cannot be removed from the distal end without breaking the applicator, thereby rendering the applicator incapable of reuse;
   a graphical user interface (GUI) display communicatively linked to the laser delivery system, the GUI display configured to display an operating status and a selectable parameter of the handpiece assembly, the selectable parameter corresponding to the operation status and output of at least one component of the handpiece assembly; and
   a processor and a non-transitory computer-readable storage medium in data communication with the processor, the non-transitory computer-readable storage medium including a process executable by the processor that enables interaction and control of the handpiece assembly and laser delivery system.

2. The system of claim 1, wherein the selectable parameters of the handpiece assembly include at least one of a laser power, and a laser pulse width.

3. The system of claim 1, wherein the selectable parameters of the handpiece assembly comprise at least one selectable favorite selected from a GUI comprising a favorites selection window or icon.

4. The system of claim 1, wherein the selectable parameters of the handpiece assembly comprise at least one selectable category selected from a GUI comprising a category selection window.

5. The system of claim 1, wherein the GUI comprises a spray parameter display configured for displaying and/or controlling spray parameters of the handpiece assembly.

6. The system of claim 1, wherein the GUI includes at least one of a power meter with selectable power level, and a laser mode display and/or selector, a selectable slider configured for modifying and/or setting at least one parameter of a procedure, and a pulse display with selectable pulse icon.

7. The system of claim 1, wherein the GUI includes an air delivery display with air setting and/or air mode.

8. The system of claim 1, wherein the GUI includes a water delivery display with water setting, and water mode icon.

9. The system of claim 1, wherein the GUI includes an auxiliary icon configured for selecting or indicating auxiliary components and/or sources providing air and/or water.

10. The system of claim 1, wherein the GUI includes a handpiece exchange icon and/or tip exchange icon configurable to install and/or swap a handpiece and/or tip of the handpiece assembly.

11. The system of claim 1, wherein the disposable applicator comprises at least one structure configured and arranged to weaken or reduce the mechanical strength or integrity of at least one coupler extending from a main body of the disposable applicator, the at least one coupler configured and arranged to at least partially secure the disposable tip to the distal end of the handpiece assembly.

12. The system of claim 11, wherein the coupler comprises a clip.

13. The system of claim 12, wherein the notch is positioned at an edge of the main body of the disposable applicator, and extends at least partially into the at least one coupler, wherein the at least one coupler is configured by the notch to break from the main body when a user removes the disposable applicator from the handpiece assembly.

14. The system of claim 1, wherein the spray mixer is positioned in a lower housing extension that curves inward so that an output of the spray mixer is guided towards an axial center of the handpiece assembly.

15. The system of claim 1, wherein the disposable applicator comprises a valve, the valve configured to couple to a connector at the distal end of the handpiece assembly.

16. The system of claim 15, wherein the valve comprises a duckbill valve.

17. An assembly comprising:
   a handpiece assembly configured to receive electromagnetic energy, an air supply and at least one fluid, and to selectively, simultaneously deliver the electromagnetic energy, the air supply and the at least one fluid to a target surface, the handpiece assembly comprising:
      a handpiece housing and a plurality of fluid lines extending through the hand piece housing, the plurality of fluid lines configured to transfer the at least one fluid from a proximal end of the handpiece assembly to a distal end of the handpiece assembly;
      a spray mixer positioned at the distal end, the spray mixer coupled to fluid lines of the plurality of fluid lines; and
      an air coupler comprising an air input port and an air delivery channel, the air coupler coupled to a housing extension of the handpiece housing, the air coupler configured to couple on-demand air to the handpiece assembly via the air input port and air delivery channel, the air delivery channel configured to deliver the air supply from the air input port to a tip of disposable, single use applicator that is coupled to a distal end of the handpiece housing, wherein the applicator is configured to break when uncoupled from the distal end thereby preventing applicator reuse.

18. The assembly of claim 17, further comprising a disposable applicator, the disposable applicator comprising at least one structure configured and arranged to weaken or have reduced mechanical strength or integrity of at least one coupler extending from a main body of the disposable applicator, the at least one coupler configured and arranged to at least partially secure the disposable tip to the distal end of the handpiece assembly.

19. The assembly of claim 18, wherein the at least one structure comprises a notch.

20. The assembly of claim 19, wherein the notch is positioned at an edge of the main body and extends at least partially into the at least one coupler, wherein the at least one coupler is configured by the notch to break from the main body when a user removes the disposable applicator from the handpiece assembly.

* * * * *